(12) United States Patent
Yodfat et al.

(10) Patent No.: US 9,173,991 B2
(45) Date of Patent: Nov. 3, 2015

(54) DEVICE FOR DRUG DELIVERY

(75) Inventors: Ofer Yodfat, Maccabim-Reut (IL); Gali Shapira, Haifa (IL)

(73) Assignee: Roche Diabetes Care, Inc., Indianapolis, IN (US)

(*) Notice: Subject to any disclaimer, the term of this patent is extended or adjusted under 35 U.S.C. 154(b) by 896 days.

(21) Appl. No.: 12/452,484

(22) PCT Filed: Jul. 2, 2008

(86) PCT No.: PCT/IL2008/000915
§ 371 (c)(1),
(2), (4) Date: Jan. 4, 2010

(87) PCT Pub. No.: WO2009/004627
PCT Pub. Date: Jan. 8, 2009

(65) Prior Publication Data
US 2010/0145303 A1  Jun. 10, 2010

Related U.S. Application Data

(60) Provisional application No. 60/958,220, filed on Jul. 2, 2007.

(51) Int. Cl.
*A61M 5/14* (2006.01)
*A61M 5/142* (2006.01)
*A61M 5/172* (2006.01)

(52) U.S. Cl.
CPC ......... *A61M 5/1408* (2013.01); *A61M 5/14228* (2013.01); *A61M 5/14244* (2013.01); *A61M 5/1723* (2013.01); *A61M 2005/14208* (2013.01); *A61M 2005/1726* (2013.01)

(58) Field of Classification Search
CPC ........... A61M 2005/14208; A61M 2005/1726; A61M 5/1408; A61M 5/14244; A61M 5/1723; A61M 5/14228
USPC ................... 604/506, 66, 151, 503
See application file for complete search history.

(56) References Cited

U.S. PATENT DOCUMENTS 3,600,135 A * 8/1971 Davis .................... 210/195.1
4,143,649 A * 3/1979 Foti ....................... 600/555
(Continued)

FOREIGN PATENT DOCUMENTS

DE         10352456 A1    7/2005
DE    202005012358 U1   10/2005
(Continued)

OTHER PUBLICATIONS

English Translation of DE 103 52 456 A1.*
(Continued)

*Primary Examiner* — Andrew Gilbert
(74) *Attorney, Agent, or Firm* — Dinsmore & Shohl LLP

(57) ABSTRACT

Delivery of more than one therapeutic fluid as a means to control symptoms of a health conditions is disclosed. More than one therapeutic fluid may be dispensed from more than one reservoir and delivered to a user's body via one or more cannula that penetrate the skin. The therapeutic fluids may be delivered by action of one or more pumping mechanisms that may be controlled by a processor in a portable, ambulatory device. The therapeutic fluids may optionally be insulin and one or more of an amylin analog, pramlintide acetate and an exenatide, and the health condition may optionally be diabetes.

30 Claims, 14 Drawing Sheets

(56) References Cited

U.S. PATENT DOCUMENTS

| | | | |
|---|---|---|---|
| 5,284,425 A * | 2/1994 | Holtermann et al. | 417/395 |
| 8,540,678 B2 * | 9/2013 | Kodgule et al. | 604/173 |
| 2007/0054851 A1 * | 3/2007 | Lin et al. | 514/12 |
| 2007/0060871 A1 * | 3/2007 | Istoc et al. | 604/65 |
| 2007/0088271 A1 * | 4/2007 | Richards | 604/151 |
| 2007/0112298 A1 | 5/2007 | Mueller et al. | |
| 2007/0191702 A1 * | 8/2007 | Yodfat et al. | 600/365 |
| 2008/0004515 A1 * | 1/2008 | Jennewine | 600/345 |
| 2008/0214916 A1 * | 9/2008 | Yodfat et al. | 600/347 |
| 2008/0215035 A1 | 9/2008 | Yodfat et al. | |
| 2008/0281290 A1 * | 11/2008 | Yodfat et al. | 604/504 |
| 2010/0298764 A1 | 11/2010 | Yodfat et al. | |
| 2014/0329319 A1 * | 11/2014 | Scott | 435/375 |

FOREIGN PATENT DOCUMENTS

| | | |
|---|---|---|
| WO | WO-2006102412 A2 | 9/2006 |
| WO | WO-2006108809 A1 | 10/2006 |
| WO | WO-2006121921 A2 | 11/2006 |
| WO | WO-2006127905 A2 | 11/2006 |
| WO | WO-2008005780 A2 | 1/2008 |

OTHER PUBLICATIONS

Ceriello, A., "Postprandial Hyperglycemia and Diabetes Complications: Is It Time to Treat?", *Diabetes*, 54:1-7 (2005).

DCCT Trial Research Group, "The Effect of Intensive Treatment of Diabetes on the Development and Progression of Long-Term Complications in Insulin-Dependent Diabetes Mellitus", *N. E. J Med.*, 329:977-986 (1993).

El-Khatib et al., "Pharmacodynamics and Stability of Subcutaneously Infused Glucagon in a Type 1 Diabetic Swine Model In Vivo", *Diabetes Tech. Therapeutics*, 9(2):135-144 (2007).

International Search Report for PCT Application No. PCT/IL2008/000915, mailed Feb. 12, 2009.

Karl et al., "Pramlintide as an Adjunct to Insulin in Patients with Type 2 Diabetes in a Clinical Practice Setting Reduced A1C, Postprandial Glucose Excursions, and Weight", *Diabetes Tech. Therapeutics*, 9(2):191-199 (2007).

Nathan et al., "Intensive Diabetes Treatment and Cardiovascular Disease in Patients with Type 1 Diabetes", *N.E. J. Med.*, 353(25):2643-2653 (2005).

Ratner, R. E., "Adjunctive Therapy with the Amylin Analogue Pramlintide Leads to a Combined Improvement in Glycemic and Weight Control in Insulin-Treated Subjects with Type 2 Diabetes", *Diabetes Tech. Therapy*, 4(1):51-61 (2002).

UKPDS Group Trial, "Tight blood pressure control and risk of macrovascular and microvascular complications in type 2 diabetes: UKPDS 38", *BMJ*, 317:703-713 (1998).

UKPDS Trial, "Intensive blood-glucose control with sulphonylureas or insulin compared with conventional treatment and risk of complications in patients with type 2 diabetes (UKPDS 33)", Lancet, 352:837-853 (1998).

Written Opinion of the International Search Authority for PCT Application No. PCT/IL2008/000915, mailed Feb. 12, 2009.

* cited by examiner

| | | LOW DOSE 5% TDD | MEDIUM DOSE 10%TDD | HIGH DOSE 15%TDD |
|---|---|---|---|---|
| LOW GI (<55) | LOW CARB (30-70) | + | | |
| | MEDIUM CARB (71-110) | + | | |
| | HIGH CARB (>111) | | + | |
| MEDIUM GI (56-69) | LOW CARB (30-70) | + | | |
| | MEDIUM CARB (71-110) | | + | |
| | HIGH CARB (>111) | | | + |
| HIGH GI (>70) | LOW CARB (30-70) | | + | |
| | MEDIUM CARB (71-110) | | | + |
| | HIGH CARB (>111) | | | + |

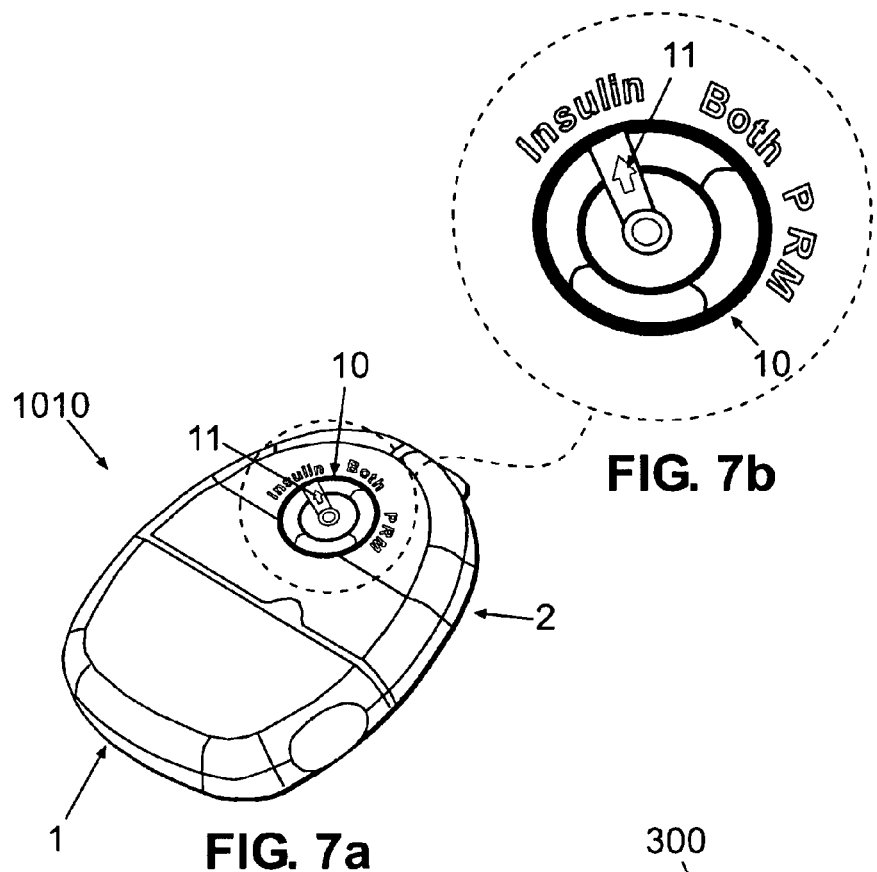
FIG. 7b
FIG. 7a
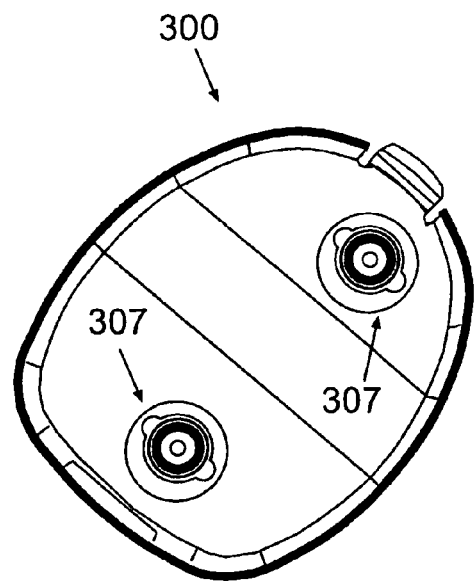
FIG. 7c

DEVICE FOR DRUG DELIVERY

CROSS-REFERENCE TO RELATED APPLICATION

The present application is a 35 U.S.C. §371 national stage entry of PCT/IL2008/000915, which has an international filing date of 2 Jul. 2008 and claims priority to U.S. Provisional Patent Application No. 60/958,220, filed on 2 Jul. 2007. The present application incorporates herein by reference the disclosure of each of the above-referenced applications in its entirety.

FIELD

The present invention relates to a devices and methods for sustained medical infusion of drugs, including but not limited to delivery of one or more injectable drugs. In some non-limiting examples, an insulin dispensing device can be coupled to a glucose monitoring device that can concomitantly deliver additional anti-diabetic injectable drugs or other drugs or substances.

BACKGROUND

Diabetes mellitus is a disease of major global importance that has increased in frequency at almost epidemic rates. The worldwide prevalence in 2006 is 170 million people and is predicted to at least double over the next 10-15 years. Diabetes is characterized by a chronically raised blood glucose concentration (hyperglycemia), due to a relative or absolute lack of the pancreatic hormone, insulin. Within the healthy pancreas, beta cells, located in the islets of Langerhans, continuously produce and secrete insulin according to the blood glucose levels, maintaining near constant glucose levels in the body.

Much of the burden of the disease to the user and to health care resources can occur due to long-term tissue complications that affect both the small blood vessels (microangiopathy, causing eye, kidney and nerve damage) and the large blood vessels (causing accelerated atherosclerosis, with increased rates of coronary heart disease, peripheral vascular disease and stroke). The Diabetes Control and Complications Trial (DCCT) has demonstrated that development and progression of the chronic complications of diabetes are greatly related to the degree of altered glycemia as quantified by determinations of glycohemoglobin (HbAlc). (DCCT Trial, *N. Engl. J. Med.* 1993; 329: 977-986, UKPDS Trial, *Lancet* 1998; 352: 837-853. BMJ 1998; 317, (7160): 703-13 and the EDIC Trial, *N. Engl. J. Med.* 2005; 353, (25): 2643-53). Thus, maintaining normolycemia by frequent glucose measurements and adjustment of insulin delivery accordingly can be quite important.

The glycemic index (GI) is a ranking system for carbohydrates based on their effect on blood glucose levels in the first two hours. Table 1 shows a few examples of foods and their GI.

TABLE 1

Glycemic index ranges and classifications for selected foods.

| Classification | GI Range | Examples |
| --- | --- | --- |
| Low GI | 55 or less | Most fruit and vegetables (but not potato), oats, buckwheat, whole barley, All-bran |
| Medium GI | 56-69 | Sucrose, basmati rice |
| High GI | 70 or more | Corn flakes, baked potato, jasmine rice, white bread, white rice, Mars bar |

An after-meal or post-prandial glycemic peak (hyperglycemia) is defined as the net rise in a patient's blood glucose concentration that occurs from before eating to the highest point after eating. The ADA goal for diabetic treatment is a glucose concentration level that is less than 180 mg dl$^{-1}$ at approximately 1-2 hrs after the start of meal. Increasing evidence suggests that postprandial hyperglycemia is a contributing factor to the development of atherosclerosis. The postprandial phase can be characterized by a rapid and large increase in blood glucose levels. The association of postprandial "hyperglycemic spikes" with the onset of cardiovascular complications has recently received much attention. Postprandial hyperglycemia can be a direct and independent risk factor for cardiovascular disease (CVD). The mechanisms through which acute hyperglycemia exerts its effects may be identified in the production of free radicals. Correcting the postprandial hyperglycemia may form part of the strategy for the prevention and management of CVDs in diabetes (*Diabetes* 2005; 54:1-7). Other, short term problems, such as for example tiredness, concentration difficulties, decreased desire to move, mood shifts, and enhanced hunger, can also be attributed to postprandial hyperglycemia. As such, prevention of post-prandial hyperglycemia can be quite important.

Currently, the strategies used by diabetic patients for prevention of post-prandial hyperglycemia are divided into lifestyle approaches and medicinal approaches. Lifestyle approaches are mainly dietary. For example, a patient's diet can be restricted to intake of food that convert slowly to glucose, such as high fiber food. Timing of insulin boluses can also help lower post-prandial hyperglycemic peaks. Medicinal approaches include agents such as exenatide (Byetta) and pramlintide acetate (Symlin).

Amylin is a second β-cell hormone that is co-localized and co-secreted with insulin in response to meals. Consequently, β-cell dysfunction in insulin-requiring subjects with type 1 or type 2 diabetes is characterized by a markedly impaired postprandial secretory response of both insulin and amylin. Amylin acts as a neuroendocrine hormone that complements the effects of insulin in postprandial glucose regulation through several centrally mediated effects that can include a suppression of postprandial glucagon secretion and a vagus-mediated regulation of gastric emptying, thereby helping to control the influx of endogenous and exogenous glucose, respectively. Amylin has also been shown to reduce food intake and body weight, consistent with an additional satiety effect. Consistent with these findings, mealtime amylin replacement, as an adjunctive therapy to insulin delivery, can improve metabolic control in diabetic subjects.

FIG. 1 shows the co-secretion of amylin and insulin in response to meals in a healthy subject. Both hormones are co-localized in the β-cells of the pancreas. β-cell dysfunction in insulin-requiring subjects with type 1 or type 2 diabetes is characterized by a markedly impaired postprandial secretory response of both insulin and amylin.

Native human amylin is typically not ideal for clinical use because of the peptide's poor solubility and propensity to aggregate. Pramlintide is a soluble, non-aggregating synthetic peptide analog of human amylin that has a potency at least equal to that of native amylin. Pramlintide in insulin-requiring subjects with diabetes has been shown, as an adjunct to insulin therapy, to correct postprandial hyperglucagonemia, slow the delivery of nutrients from the stomach to the small intestine, and, concomitantly, improve postprandial glucose excursions (*Diab. Tech. Therp.* 2002; 4(1):51-61).

Pramlintide can be injected subcutaneously with a standard insulin syringe, rendering the dosage flexible. For weight loss, maximum doses are administered and for normalizing post-prandial glucose levels, lower doses are indicated. The dosing recommended by the manufacturer for normalizing post-prandial glucose levels are the following: starting with 2.5 units and increasing to 5 units, then 7.5 units, and 10 units before each meal if no nausea is encountered for three consecutive days.

FIG. 2 shows mean (±SE) values for seven-point glucose profiles performed before (open circles) and after 6 months (solid circles) of pramlintide therapy in patients with type 2 diabetics on insulin therapy. The blood glucose concentrations were assessed within 0.5 h before and 1.5-2 h after breakfast, lunch, and dinner and at bedtime. It can be seen that both fasting and postprandial glucose concentrations were significantly reduced compared to baseline (P<0.05). (*Diabetes Technology & Therapeutics* 2007; 9 (2): 191-99.)

Insulin pumps can be used to deliver rapid acting insulin to a diabetic patient 24 hours a day through a catheter placed under the skin (subcutaneously). The total daily insulin dose can be divided into basal and bolus doses. Basal insulin can be delivered continuously, semi-continuously, or periodically over 24 hours, thereby maintaining the blood glucose concentration level (namely, blood glucose levels) within a normal, desirable range between meals and overnight. Diurnal basal rates can be pre-programmed or manually changed according to various daily activities. Insulin bolus doses can be delivered before or after meals to counteract carbohydrates loads or during episodes of high blood glucose concentration levels.

SUMMARY

In a first aspect, a portable therapeutic fluid delivery device has a form factor that permits ambulatory use by a patient and includes a first reservoir for containing a first therapeutic fluid, a second reservoir for containing a second therapeutic fluid, at least one cannula disposed to penetrate the patient's skin to deliver the first and/or the second therapeutic fluid subcutaneously at a dosing rate and being in fluid communication with the first and/or second reservoir, at least one pumping mechanism that delivers the first therapeutic fluid from the first reservoir at a first dosing rate and delivers the second therapeutic fluid from the second reservoir at a second dosing rate to the at least one cannula and into the patient, and a processor that controls the at least one pumping mechanisms.

In a second interrelated aspect, an infusion system for dispensing at least insulin and a second anti-diabetic agent into a patient's body includes a drug dispensing means that comprises a first reservoir and a first dispensing means for dispensing insulin for infusion into the patient's body and a second reservoir and a second dispensing means for dispensing the second anti-diabetic agent for infusion into the patient's body; a sensing means that measures a glucose level in the patient's body; and a processor that receives data regarding the glucose level from the sensing means and controls the drug dispensing means to regulate the dispensing of insulin and the anti-diabetic agent according to the glucose level.

In a third interrelated aspect, a method for delivery of a therapeutic fluid to a user from a portable, ambulatory device, includes delivering a first therapeutic fluid from a first reservoir of the device to the user via at least one cannula at a first dosing rate, delivering a second therapeutic fluid from a second reservoir to the user via the at least one cannula at a second dosing rate, and controlling the first dosing rate and the second dosing rate to affect a diabetes state of the user. The controlling is performed by a processor in the portable, ambulatory device.

Various additional features of these and other aspects that are disclosed herein can optionally include, but are not limited to, the following. The at least one cannula can include a first cannula in fluid communication with the first reservoir and a second cannula in fluid communication with the second reservoir. The first dosing rate can be different from the second dosing rate. The at least one pumping mechanism can include a first pumping mechanism and a second pumping mechanism wherein the first pumping mechanism delivers the first fluid from the first reservoir and the second pumping mechanism delivers the second fluid from the second reservoir. A remote control unit can be included and itself include a user interface for entering commands and/or receiving data from the processor. A wireless communication module can be included in the portable device for communication between the processor and the remote control unit. A sensing apparatus can be included that measures at least one health related parameter of the patient. The sensing apparatus can be a glucose monitor that at least semi-continuously measures blood glucose concentration data for the patient and communicates the blood glucose concentration data to the processor and the processor can optionally control the first and/or the second dosing rate in response to the blood glucose concentration data. The first therapeutic fluid can be insulin, and the first dosing rate can include a basal dosing component and/or a bolus component. The bolus component is determined based on data from the sensing apparatus. If the sensing apparatus provides glucose concentration data, the processor can control the first and/or the second dosing rate in response to the glucose concentration data. The second therapeutic fluid can optionally be a glucagon, an exenatide, or an amylin analog which can optionally be pramlintide acetate. The first and/or the second dosing rate can be based on expected calorie and/or carbohydrate intake by the patient. Delivery of the second therapeutic fluid can optionally be for prevention of post prandial hyperglycemia and/or user weight loss. The second therapeutic fluid can be pramlintide, and the dosage of the pramlintide can be 10% of a total daily dose of insulin (TDD) before each meal. A tolerability of the user for the first and/or the second dosing rates can be determined by the processor.

The portable therapeutic fluid delivery device can optionally further include at least one disposable part and a reusable part that mate with each other to form a dispensing patch unit. The at least one disposable part can include the first reservoir and the second reservoir, and the reusable part can include the processor and a pumping mechanism of at least one of the first and the second pump mechanisms. At least one housing can be included to contain the first reservoir, the second reservoir, the at least one pumping mechanism, and the processor, and the portable device can also include a cradle unit with an attachment side for securing to the skin and a mating side that connects to the at least one housing. The at least one pumping mechanism can include a piston-type displacement pumping mechanism that comprises a propelling plunger and/or the at least one pumping mechanism can include a peristaltic pumping mechanism. At least one of the first and the second reservoirs can be collapsible such that it changes volume according to the volume of the therapeutic fluid contained therein. The first reservoir can be coupled to a first housing and the second reservoir can be coupled to a second housing. Alternatively, the first reservoir and the second reservoir can be coupled to a single housing. One or more buttons can be included via which the patient can adjust the first and/or the second dosing rate.

Various features of the current subject matter can provide one or more benefits and for advantages that can include, but are not limited to provision of a device that can dispense insulin and one or more additional injectable anti diabetic drugs (such as for example an amylin analog like pramlintide) to prevent post-prandial hyperglycemia and achieve a better glycemic control for a diabetic patient. The current subject matter can also be used in other applications in which delivery of more than one therapeutic fluid, formulation, or other substance to a patient or subject is desirable. One or more sensing apparati or other sensing data streams can be incorporated with the current subject matter to provide real time or near real time measurement of one or more factors that might impact the desired dose of the one or more therapeutic fluids to be delivered. Automated control, or alternatively automated alerting that user action is required can be provided in response to these measurements to allow prompt dosing of a therapeutic fluid in response to a measured body condition, such as for example an elevated or depressed blood glucose level. A continuous subcutaneous insulin infusion device can be provided that infuses basal insulin dosages and pre-meal bolus insulin dosages. In addition, the infusion device can comprise a pramlintide subcutaneous infusion mechanism that allows the user to administer the amylin analog before a meal and prevent post-prandial hyperglycemia. Devices according to various implementations of the current subject matter can be miniature, discreet, and economical for the user and highly cost effective. Relatively expensive components of such devices can optionally be provided in a reusable part that mates with a disposable part that contains relatively inexpensive components that can be discarded and replaced more frequently.

The details of one or more variations of the subject matter described herein are set forth in the accompanying drawings and the description below. Other features and advantages of the subject matter described herein will be apparent from the description and drawings, and from the claims.

For the purposes of promoting an understanding of the subject matter described herein, which can include one or more features and variations as described below, references may be made to specific implementations having discrete feature sets. The terminology used herein is for the purpose of describing particular implementations only, and is not intended to limit the scope of either the disclosed subject matter or of the particular inventions that are claimed below. For example, references to the delivery of insulin and/or the treatment of diabetes are intended to serve as illustrative examples of broader inventive concepts. Use of other therapeutic fluids, either in addition to or in place of insulin, as well as materials and apparatuses compatible with the same, are within the contemplated scope of the current subject matter. Additionally, as used throughout this disclosure, the singular articles "a," "an," and "the" are intended to include both singular and plural references unless the context clearly indicates otherwise. Thus, for example, a reference to "a tube" includes a plurality of such tubes, as well as a single tube, and any equivalents thereof.

Throughout this description, including the foregoing description of related art, any and all publicly available documents described herein, including any and all U.S. patents, are specifically incorporated by reference herein in their entirety. Descriptions of related art are not intended in any way as an admission that any of the documents described therein, including pending applications for United States patent, are prior art to the present invention. Moreover, the description herein of any disadvantages associated with the described products, methods, devices, systems and/or apparatus is not intended to limit the scope of the current subject matter. Indeed, aspects of the current subject matter can include certain features of the described products, methods, devices, systems and/or apparatus without suffering from their described disadvantages.

DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

FIG. 7a, FIG. 7b, FIG. 7c, and FIG. 7d are schematic diagrams that show a cradle unit and dispensing unit of a patch infusion device;

Wherever possible, the same reference numbers have been used throughout the drawings to refer to the same or like parts.

DETAILED DESCRIPTION

Figure 1:
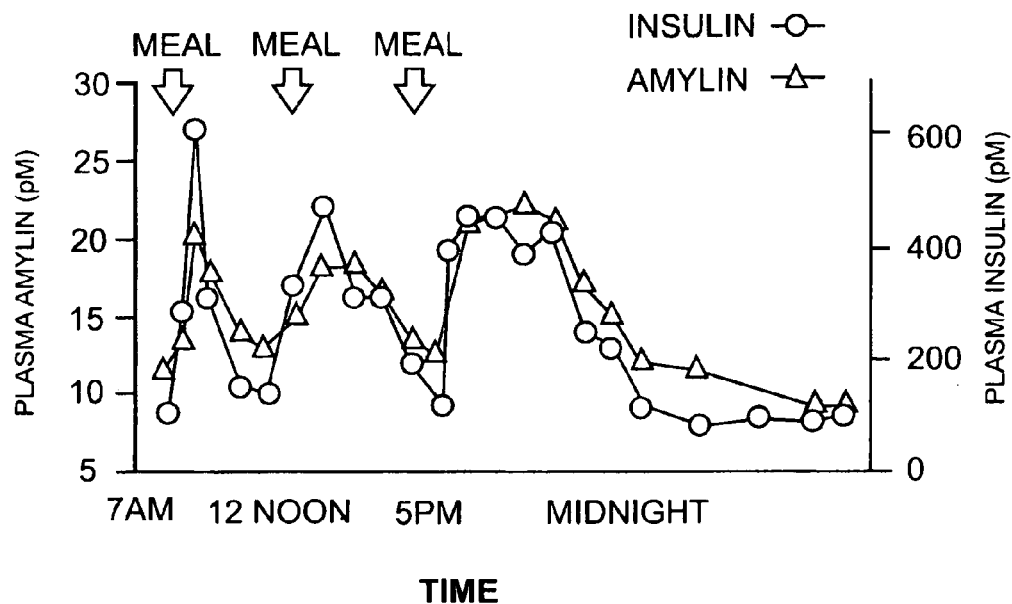
FIG. 1 is a chart that shows co-secretion of amylin and insulin in response to meals in a healthy subject.
Figure 2:
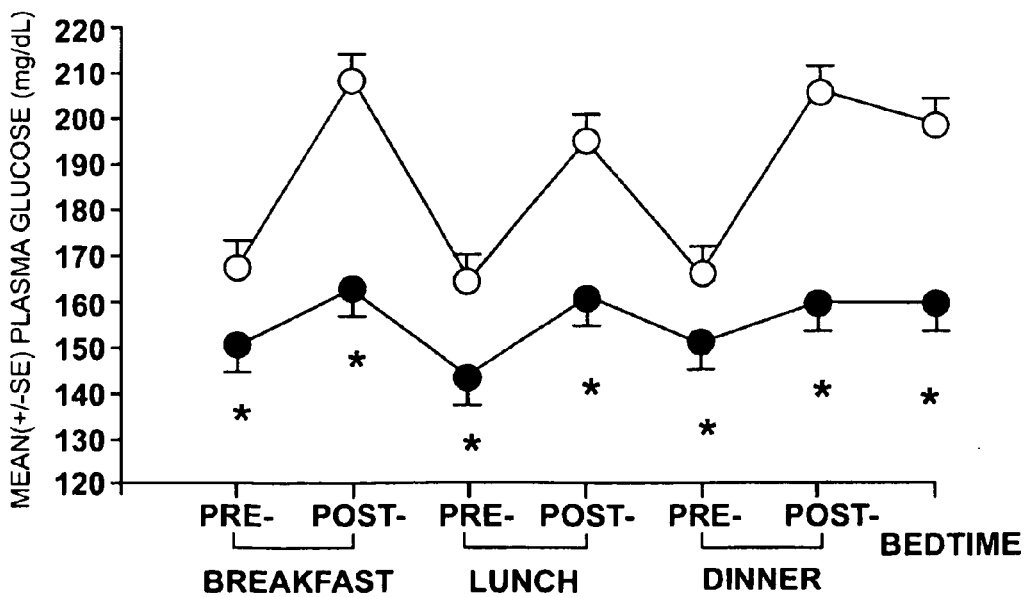
FIG. 2 is a chart that shows the decrease in fasting and post prandial glucose achieved with addition of pramlintide therapy.

Currently, pump users who use additional diabetic drugs that are administered to the subcutaneous tissue (such as for example an amylin analog like pramlintide), cannot deliver the drugs concomitantly and are required to inject the non-insulin drug or drugs separately, a process that requires additional pricking which can often lead to poor compliance with a treatment regimen. Accordingly, there is a need for devices and/or methods capable of delivering more than one active substance into the body to achieve better glycemic control. The subject matter described herein can provide devices, apparatuses, systems, methods, techniques, and the like with advantages of that include, but are not limited to miniature, discreet, economical for the users and highly cost effective, that can deliver more than one active substance into the body to achieve better glycemic control. Devices according to the current subject matter can include a miniature infusion patch unit that can be adhered to the skin and that can deliver more than one active substance into the body. Such infusion patch units can be remotely controlled and can deliver more than one active substance into the body.

In some implementations, the dispensing device includes a sensor for measuring glucose levels. Such a sensor that can continuously monitor glucose level is provided, for example, in co-pending and co-owned U.S. application Ser. No. 11/989,678, filed 28 Jan. 2008 and entitled "Fluid delivery system with optical sensing of analyte concentration levels," the disclosure of which is hereby incorporated by reference. In some implementations, a dispensing patch unit can subcutaneously dispense glucagon, in addition to other diabetic agents, such as for example insulin. Endogenous glucagon secretion can be somewhat compromised in type 1 diabetes, since the (absent) β-cells are also themselves sensors for BG concentration (*Diab. Tech. Therap.* 2007; 9(2): 135-144). Glucagon is released whenever the patient is hypoglycemic or when hypoglycemia is impended (rapidly declining blood glucose levels), and acts as a counter-agent to insulin. The glucagon acts rapidly to prevent blood glucose excursions (i.e. deviation from blood glucose target zone) and thereby achieve normoglycemia. The infusion patch unit that can dispense glucagon and insulin can optionally work in a closed loop system.

The optimal amylin analog (for example pramlintide or the like) dosage can optionally be based on postprandial glucose measurements. In some examples, the goal of the ADA and the DCCT can be to keep glucose peak 2 hours after a meal below 180 mg/dL. If the goal is not reached, the device can recommend increasing the dosage.

Various implementations of the currently disclosed subject matter can provide infusion devices that include a miniature skin adherable infusion patch unit (also referred to herein as a "dispensing patch") that can in some examples be remotely controlled by a remote control unit. The dispensing patch can be discreet and free of inconvenient tubing and can dispense one or more therapeutic fluids, such as for example insulin and/or an amylin analog such as pramlintide from one or more reservoirs via one or more delivery tubes. Fluid motion can be urged by one or more pumping mechanisms, including but not limited to peristaltic pumps, piston-type displacement pumps, and the like. The dispensing patch can in some examples include a disposable part and a reusable part. The reusable part can optionally contain relatively expensive components of the dispensing patch (such as for example a peristaltic pump wheel, driving mechanism and electronics) and the disposable part can optionally contain relatively less expensive components (such as for example a delivery tube, reservoir, and the like). In this manner, a device can have relatively low ongoing operating costs for a user while being highly profitable for manufacturers and payers.

Dispensing patch units consistent with various aspects of the current subject matter can in some variations and implementations include one or more peristaltic pumping mechanisms (peristaltic pump). The peristaltic pump can optionally include a rotatable structure such as a wheel that includes one or more rollers, a stator and a delivery tube. The wheel and rollers can in some variations be located within a reusable part of the dispensing patch and a delivery tube and stator can be located within a disposable part. After disposable and reusable parts are properly paired, the wheel can be rotated and the rollers can squeeze the tube against the stator. Fluid delivery can thereby be maintained in the direction of rotation of the wheel. In some variations, a deformable reservoir that collapses and decreases in volume as fluid is withdrawn therefrom can be used in conjunction with a peristaltic pumping mechanism. Other variations and implementations can include a piston-type displacement pumping mechanism that includes a rigid or semi-rigid reservoir body and a plunger mechanism that can be moved to urge fluid out of the reservoir body.

FIG. 3 shows an implementation of the current subject matter that includes a dispending patch 1010 that can deliver two therapeutic fluids. The dispensing patch 1010 can be adhered to the user's skin 5. A remote control unit 1008 can communicate with the dispensing patch unit 1010, thereby allowing programming, user inputs and data acquisition. Manual inputs of one or more of the therapeutic fluids deliverable from the dispensing patch unit 1010 can be carried out by buttons 10 located on the dispensing patch unit 1010. The dispensing patch unit 1010 can include two housings 1001, 1002 that contain reusable 1 and disposable 2 parts, respectively.

The disposable part 2 of the dispensing patch unit 1010 can contain two reservoirs 3 and 33. If the dispensing patch unit 1010 is used to treat diabetic symptoms, a first reservoir 3 can contain insulin and a second reservoir 33 can contain pramlintide. Each reservoir can be associated with a cannula 6, 66 that each penetrate the skin 5 to allow separate delivery of the two therapeutic fluids (for example insulin and pramlintide). The dispensing patch unit 1010 can be directly attached to the user's skin by adhesive means or some other attachment means such as for example a strap, or can be attached to a dedicated cradle unit that is adherable to the user's skin 5 and allows connection and disconnection of the patch unit 1010 as described in U.S. Provisional Patent Application No. 60/876,679, which is incorporated herein by reference in its entirety.

The relatively cheap components of the device, such as for example the two cannulae 6 and 66 can optionally reside in the disposable part 2, while the relatively expensive components can optionally reside in the reusable part 1. The delivered fluids can be insulin and any additional injectable therapeutic fluid that can be delivered to the subcutaneous tissue.

Manual inputs carried out by pressing at least one button 10 on the patch unit can cause delivery of a discrete amount of therapeutic fluid (e.g. insulin or pramlintide). According to some implementations, each pressing of the button can optionally deliver a predetermined dosage or quantum of the therapeutic fluid, and the user may determine the amount of quanta to be delivered by consecutive pressing of the button. Where delivery of pramlintide is carried out via a single pressing of the manual button 10), the delivered dose can optionally be 10% of the user's TDD of insulin. In some implementations, the button can comprise a pointer that may point to several different dosages (or different number of pramlintide quanta) and the user can determine the amount of quanta to be delivered by adjusting the pointer and then pressing of the button. The device can optionally recommend the optimal dosage of pramlintide. The user can then be able to accept or reject the recommendation. Alternatively, the dosage may be increased without user interface.

The dosage can be expressed as absolute values (e.g. each quantum or button press is equivalent to 2 units of pramlintide). Alternatively, the dosage can be expressed as percentage of TDD of insulin (e.g. each quantum or button press is equivalent to 5% of TDD).

Figures 3A, 3B:
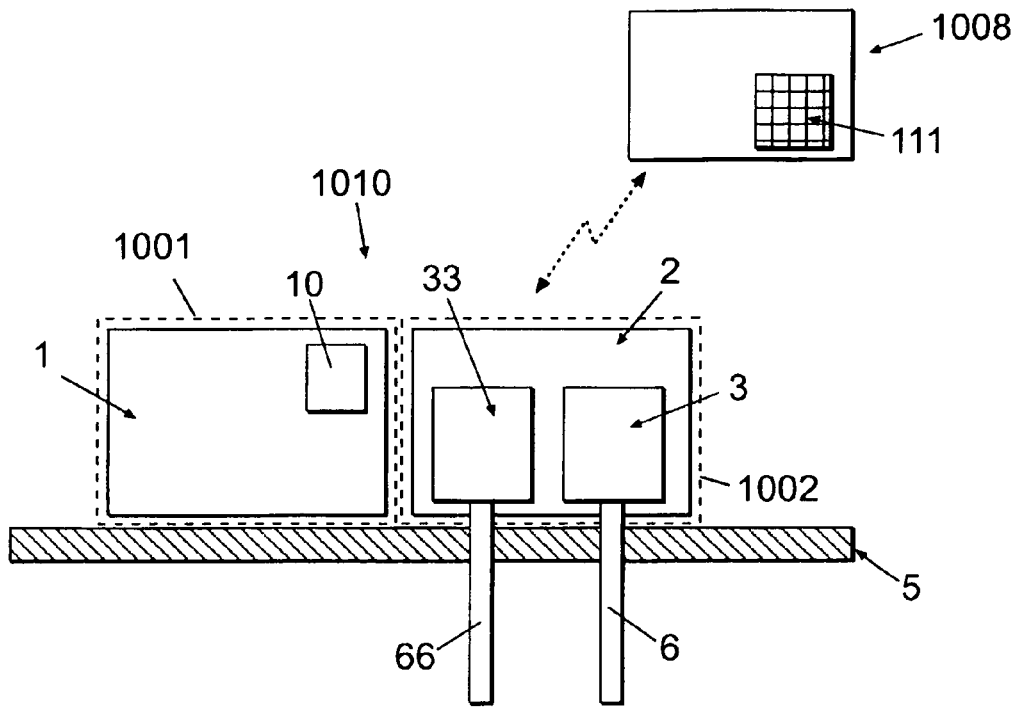
FIG. 3a is a schematic diagram that shows an infusion device comprising a dispensing unit that can deliver two therapeutic fluids as well as a remote control unit.
FIG. 3b is a table diagram that shows an example of a dosing recommendation of pramlintide when given as an adjunctive therapy to insulin.

Pramlintide dosages may be delivered using the remote control unit 1008 of the device. According to some implementations, the user may command administration of any dosage by inputting the value into the remote control unit. Alternatively the user may select a number of quanta of pramlintide to be delivered. In various implementations, the user may select the pramlintide dosage in accordance with the glycemic index (GI) and/or the carbohydrate load of the meal. In some implementations the pramlintide dosage may be chosen from within a grid 111. An example of such a grid is shown in FIG. 3b.

Figure 4A:
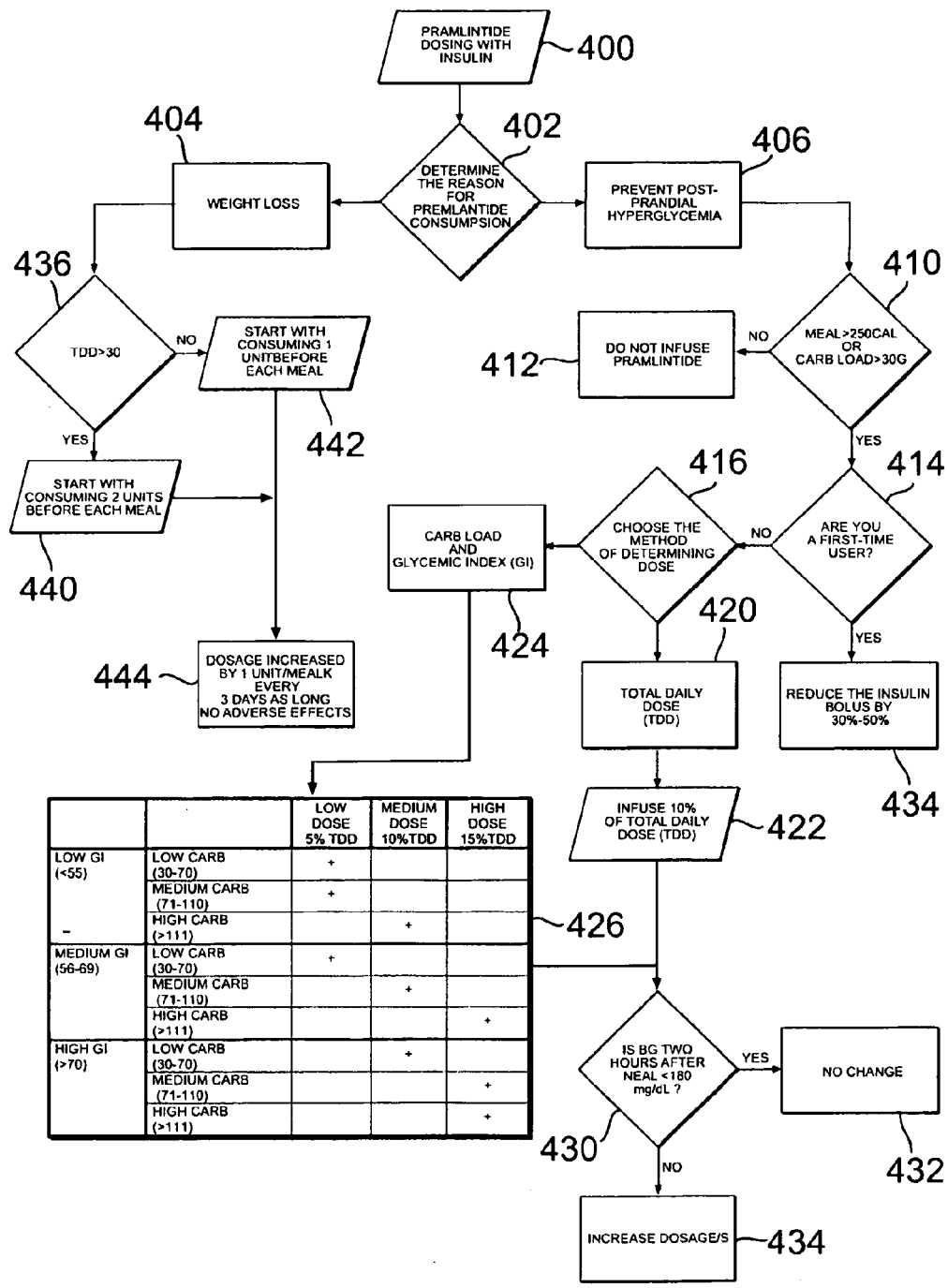
FIG. 4a and FIG. 4b are process flow diagrams illustrating methods for delivering therapeutic fluids for patient treatment.

FIG. 4a is a process flow diagram showing an example of dosing recommendations for amylin analog (Pramlintide) used as an adjunctive therapy to insulin. Dosing of pramlintide 400 is dependent on intended use. The intended use is determined at 402. For weight loss at 404, maximum doses can be preferred, while lower doses can be preferable when the goal is to normalize post-meal glucose levels at 406.

In some implementations, a suitable dosing regime can include starting with a small dose, such as for example 2.5 units, and increasing the dose progressively, for example to 5 units, then 7.5 units, and 10 units, before each meal if no nausea is encountered for some set period of time, such as for example three days. However, different patients can require different doses, and therefore pramlintide doses are preferably individualized. According to some implementations, the dosage of pramlintide can be based on the amount of carbohydrates the user plans to consume and on the GI of the contemplated carbohydrates. The user can insert (for example into the remote control) the amount of carbohydrates and their correspondent GI. The optimal dosage of pramlintide for the specific user can then be delivered at 410. In one example if the meal is expected to be smaller than a preset threshold (e.g. 250 Cal or 30 g carbohydrate), pramlintide may not be required at 412. If this threshold or some other predetermined threshold is expected to be exceeded based on user input, pramlintide can be delivered.

If pramlintide is determined to be required a determination can be made at 414 whether the user is a first time user. If not, a method of determining an appropriate dose can be chosen at 416. One option, at 420 is an insulin total daily dose (TDD) method in which the device delivers a discrete predetermined dosage of pramlintide at 422, for example in multiples of some base dosage, which is calculated as percentage of TDD. In this example, 10% of the user's insulin TDD can be delivered as a bolus. The bolus can optionally be delivered by pressing the bolus button or buttons on a dispensing patch unit 1010. For example if the TDD is 50 IU of insulin, each button press can deliver 5 units of pramlintide (3 presses=15 units of pramlintide). Bolus deliveries can also and/or alternatively be controlled using a remote control 1008. An alternative method of determining the dose is according to meal glycemic index (GI) and carbohydrate content at 424. A user can deliver the calculated exact amount of pramlintide in accordance with a table 426 such as that shown in FIG. 3b. Delivery of the selected bolus can optionally be commanded by the remote control.

The optimal pramlintide dosages can also be based on postprandial glucose measurements at 430. In one example, the goal can be to keep the blood glucose peak 2 hours after a meal below 180 mg dL$^{-1}$. If the goal is reached at 432, it can be determined that the dosage or dosages are adequate for the user. If the goal is not reached at 434, the dosage or dosages can be adjusted before the following meals.

If the use of pramlintide is initiated (i.e. first time user) at 434, mealtime insulin with the first dose of pramlintide can optionally be reduced by some amount, for example by approximately 30-50%, to decrease the risk of hypoglycemia. Once pramlintide tolerability is established, basal and mealtime insulin doses can be adjusted, based on automatically or self-monitored bodily glucose values. Alternatively, the dosage may be increased without user interface.

For weight loss at 404, larger amounts of pramlintide may be needed. The TDD can be determined at 436. If TDD is greater than some threshold, for example 30 U, at 440, the user can be initiated with 2 units before the two or three largest meals of the day. If TDD is less than the threshold at 442, the user can be initiated with 1 unit per meal. The dosages can then be increased by 1 unit per meal every three days as long as nausea is not present at 444.

Figure 4B:
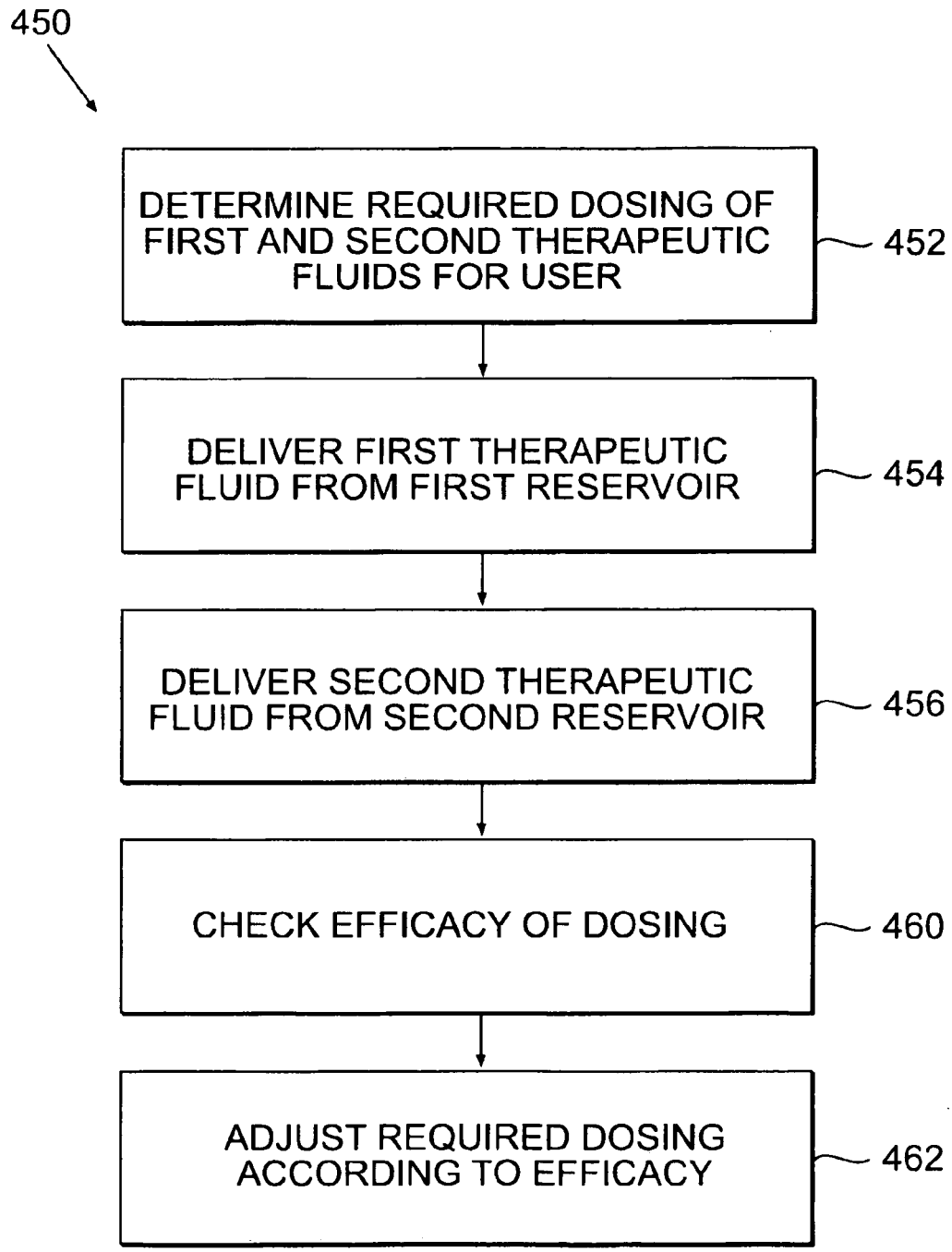

FIG. 4b is a process flow chart 450 that shows a method for monitoring and controlling blood glucose levels. At 452, a determination is made of required dosings of a first therapeutic fluid and a second therapeutic fluid for a user. In some implementations, insulin can be the first therapeutic fluid and an amylin analog such as pramlintide can be the second therapeutic fluid. The required dosing can be based on input data that can in some implementations optionally include data from a sensor that monitors one or more body chemistry indicators and/or activity data from a user that are input via a user interface. Such a user interface can include buttons on a delivery device, a remote control device, or the like, possibly (although not limited to) those described herein. At 454, the first therapeutic fluid is delivered from a first reservoir. At 456, the second therapeutic fluid is delivered from a second reservoir. At 460, the efficacy of the dosing of the two therapeutic fluids is determined. In the example where the therapeutic fluids are insulin and pramlintide and continuous, discrete or semi-continuous monitoring of blood glucose is available, the determination of efficacy can include a determination of whether the patient's blood glucose level remained within a target range. Alternatively or in addition, user inputs regarding his/her perceptions or feelings can be used—for example if the user feels nauseous, light headed, or otherwise experiences symptoms of improperly elevated or depressed blood glucose, he/she can indicate this occurrence via a user interface such as buttons and/or a remote control. The required dosing can be adjusted based on the efficacy of the previous dosing. Dosing of the two fluids need not both be continuous. For example, insulin can be delivered at a basal level with occasional boluses while an amylin analog can be delivered as boluses timed to measured and/or anticipated excursions of blood glucose outside of desired ranges.

Figure 5:
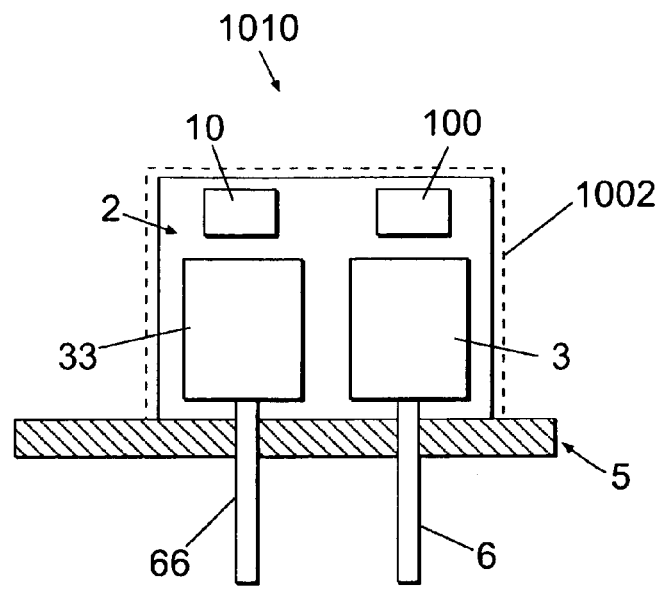
FIG. 5 is a schematic diagram that shows a patch infusion device for delivering two therapeutic fluids that includes a housing having a disposable part.

FIG. 5 shows a dispensing patch unit 1010 for delivering two therapeutic fluids. In some implementations, such a dispensing patch unit 1010 can be adhered to the user's skin 5. The dispensing patch unit 1010 can include one housing 1002 that further includes a disposable part 2. The dispensing patch unit 1010 can include a first reservoir 3 and a second reservoir 33, one for each therapeutic fluid. In some examples, the two fluids can be insulin and an amylin analog. The first reservoir 3 is associated with a first cannula 6 and the second reservoir 33 is associated with a second cannula 66. the two cannulae 6 and 66 each that penetrate the skin 5 to allow separate delivery of the two therapeutic fluids. Two bolus buttons 10 and 100 can be included on the dispensing patch unit 1010 to control boluses of each of the therapeutic fluids individually. For example, for insulin and an amylin analog, each button can be programmed to release a required, discrete pre-meal dosage.

In some implementations, insulin delivered via a dispensing patch unit 1010 such as those described herein can be rapid acting (such as for example Humalog) and be given as a pre-meal "food bolus". Long acting insulin (such as for example Glargine, Detemire, etc.) can be injected once a day to meet the basal insulin requirements. The long acting insulin can be delivered via the same cannula as the rapid acting insulin, as detailed below in regards to FIG. 7 or separately at a different remote injection site.

In some implementations, several discrete bolus dosages can be selected and administered for each drug (e.g. low, medium and high dose). The selected bolus dosage of each drug is in accordance with numerous variable parameters such as carbohydrate load of the meal, the glycemic index of the carbohydrates in the meal, and contemplated physical activity. According to one such implementation, the dosages may be divided into predetermined quanta and each press on the bolus button may increase the dosage by one quantum.

Figure 6A:
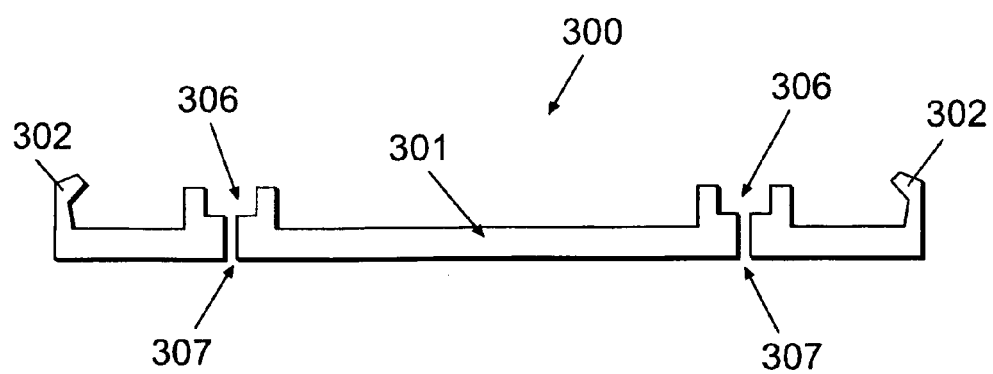
FIG. 6a, FIG. 6b, and FIG. 6c are schematic diagrams that show a patch infusion device including a cradle unit and a dispensing unit.
Figure 6B:
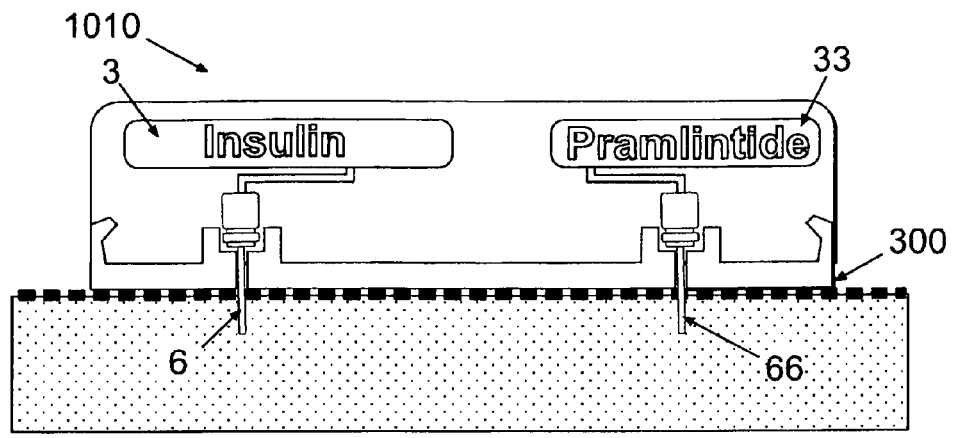
Figure 6C:
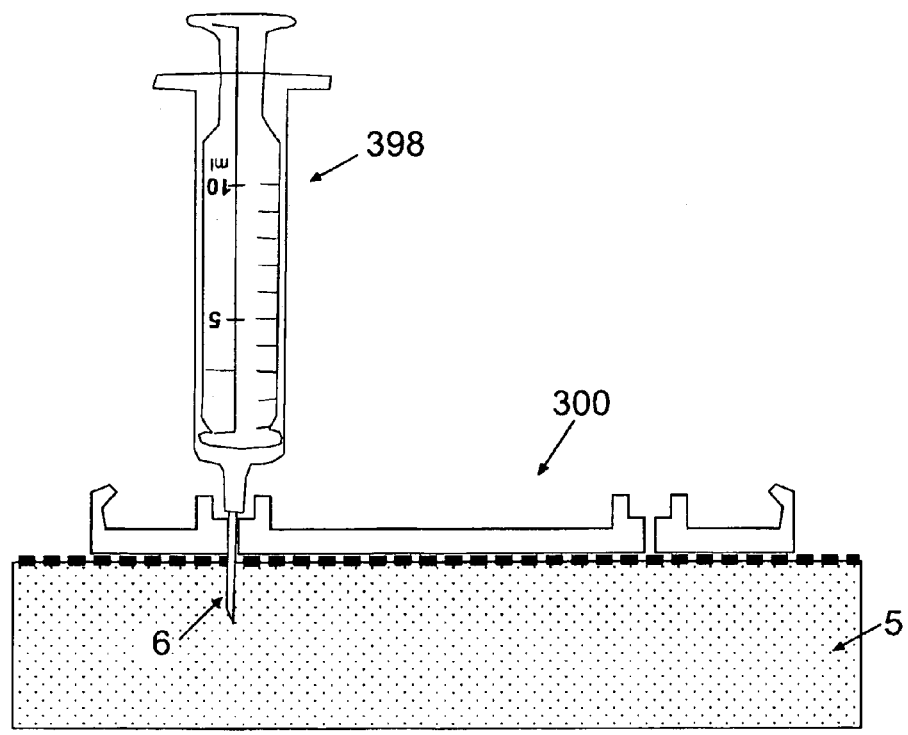

FIG. 6a, FIG. 6b, and FIG. 6c show dispensing patch units 1010 that include a cradle 300 unit and a dispensing patch unit. FIG. 6a shows the cradle 300 unit of the dispensing patch unit 1010. The cradle 300 can be a flat sheet with adhesive layer to be facing the skin and carrying a connection device or other connecting means on its upper side that allows connection and disconnection of the dispensing patch unit 1010. Upon insertion of one or more cannula 6 and 66, the cradle 300 remains adhered to the skin. The cradle 300 anchors the cannulae 6 and 66 and allows connection to the dispensing patch unit 1010. The well can be a tubular protrusion emerging upwardly from the cradle to allow alignment with the outlet port of the dispensing unit and appropriate connection between the needle and the dispensing unit as required for proper fluid delivery to the body.

FIG. 6a shows a cradle unit 300 with a cradle base 301, wells 306 and openings 307 that can accept cannulae, and anchoring latches 302 for the connection and disconnection of the dispensing unit. FIG. 6b shows the cradle unit 300 connected to the dispensing unit. The dispensing unit can include two reservoirs 3 and 33 associated with the two cannulae 6 and 66, where each reservoir 3 and 33 contains a different therapeutic fluid. For example, the first reservoir 3 can contain insulin and the second reservoir 33 can contain pramlintide as shown in FIG. 6b.

As noted above, insulin delivered via the patch infusion device can in some implementations be rapid acting insulin (such as for example Humalog) given as a pre-meal "food bolus". Long acting insulin (such as for example Glargine (Lantus), Detemire, etc.) can be injected once a day to meet the basal insulin requirements. In some variations, the long acting insulin injection can be given via a syringe 398 (for example a piston-type displacement pump) via the same cannula 6 used for delivery of the rapid acting insulin, with the dispensing unit is disconnected, as shown in FIG. 6c.

Figure 7D:
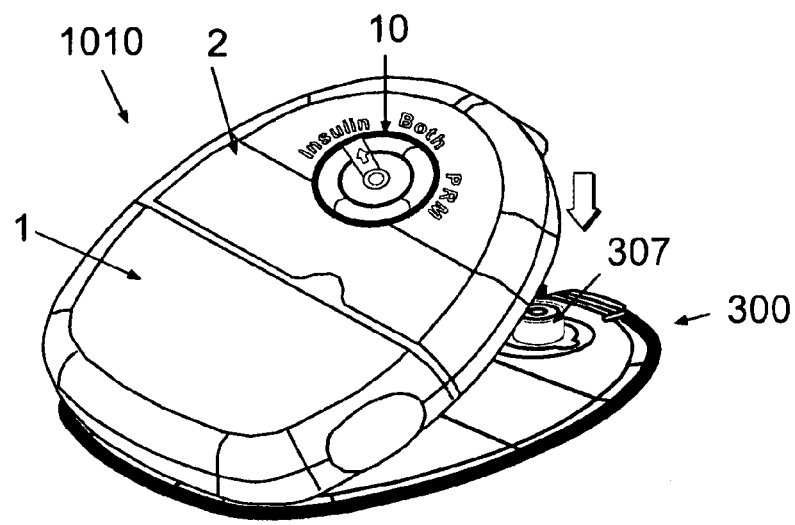

FIG. 7a, FIG. 7b, FIG. 7c, and FIG. 7d show another illustrative implementation of a cradle unit and dispensing patch unit. FIG. 7a shows a reusable part 1 and a disposable part 2 of the dispensing patch unit 1010. A button 10 that includes a pointer 11 is located on the disposable part 2. FIG. 7b shows the button 10 with the pointer 11. In this example, if the user wishes to administer a bolus of insulin alone, he/she can point the pointer 11 to "insulin" and press the button 10. If the user wishes to administer a bolus of pramlintide alone, he/she may point the pointer 11 to "PMN" and press the button 10. If the user wishes to administer simultaneously a bolus of pramlintide and a bolus of insulin, he/she may point the pointer 11 to "both" and press the button 10. FIG. 7c shows a top view of the cradle unit 300 with two openings 307. One opening 307 can be used for insulin infusion and the other opening 307 can be used for pramlintide infusion. FIG. 7d shows the connection of the cradle unit 300 and the dispensing patch unit 1010.

Figure 8:
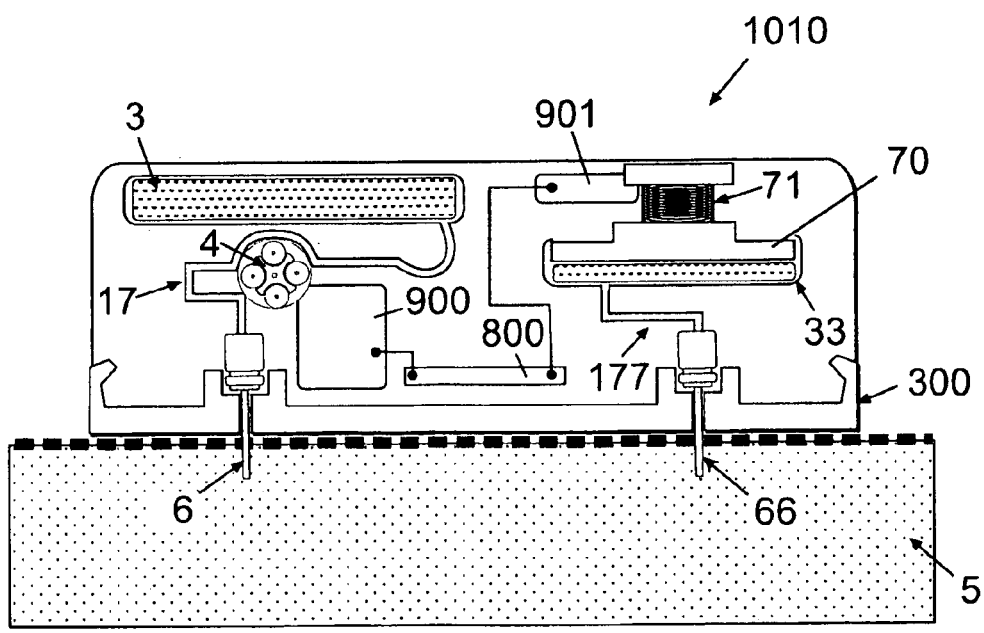
FIG. 8 is a schematic diagram that shows a patch unit with a peristaltic pump as a first driving mechanism and a piston-type displacement pump as a second driving mechanism.

FIG. 8 shows an implementation of a dispensing patch unit 1010 in which the driving mechanism for delivery of a first therapeutic fluid (for example insulin) is a peristaltic pump and the driving mechanism for delivery of a second therapeutic fluid (for example an amylin analog such as pramlintide) is a piston-type displacement pump. The first therapeutic fluid can be infused via a first cannula 6, connected to a first delivery tube 17 that is further connected to a first reservoir 3. A peristaltic pump 4 drives the first therapeutic fluid into the subcutaneous layer 5. The second therapeutic fluid can be infused from a second reservoir 33 equipped with a piston-type displacement pump that includes a propelling plunger 70 and spring 71. The second therapeutic fluid can flow via a second delivery tube 177 and second cannula 66 to the subcutaneous layer 5. The driving mechanism 900 of the peristaltic pumping mechanism 4 that delivers the first therapeutic fluid; and the driving mechanism 901 of the piston-type displacement pumping mechanism are connected to an electronic components board 800. In some implementations the piston-type displacement pumping mechanism can include a reservoir 33, propelling plunger 70 and spring 71. Alternatively or in addition, both of the pumping mechanisms can include a single driving mechanism (e.g. DC-motor, stepper motor, and the like). The pumping mechanism 900 and 901 can also optionally include a separate driving mechanism (e.g. DC-motor, stepper motor, and the like), including possibly one for each pumping mechanism. According to one implementation, the piston-type displacement pump can be manually operated, for example by manual working of the propelling plunger 70.

Figure 9:
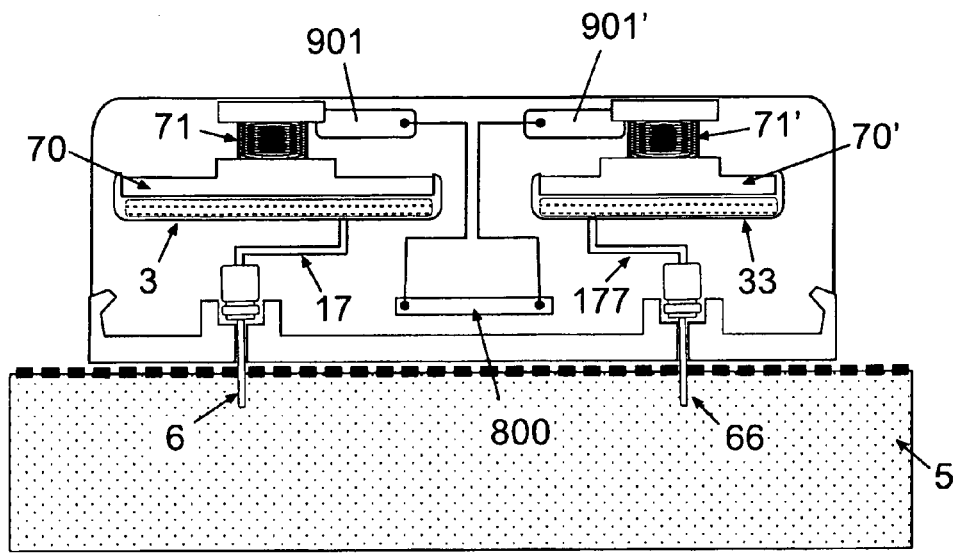
FIG. 9 is a schematic diagram that shows a patch unit in which the driving mechanism of both therapeutic fluids (such as for example insulin and pramlintide) is a piston-type displacement pump.

FIG. 9 shows a dispensing patch unit 1010 in which the pumping mechanisms for delivery of both the first and the second therapeutic fluids (for example insulin and an amylin analog such as pramlintide) are both piston-type displacement pumps. Each of the two therapeutic fluids can be infused from a reservoir 3 and 33 that includes a propelling plunger 70 and 70' and spring 71 and 71' via a delivery tube 17 and 177 and cannula 6 and 66 to the subcutaneous layer 5. The pumping mechanisms 901 and 901' of both piston-type displacement pumps can be connected to an electronic components board 800. In some implementations, both piston-type displacement pumps can be manually operated. In other implementations, the first therapeutic piston-type displacement pump can be controlled by a driving mechanism and the piston-type displacement pump of the second therapeutic fluid can be manually operated.

Figure 10:
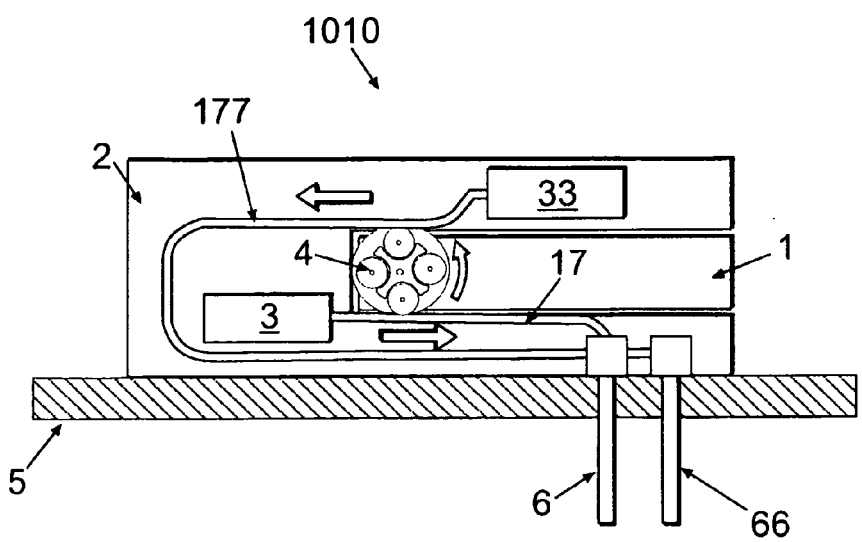
FIG. 10 is a schematic diagram that shows a two-fluid infusion device in which each fluid is delivered by an independent cannula, tube and associated reservoir, used a shared peristaltic pump.

FIG. 10 shows an implementation of a dispensing patch unit 1010 in which the pumping mechanism for delivery of both the first and the second therapeutic fluids is a peristaltic pump. Each fluid delivery path can include an independent cannula 6 and 66, delivery tube 17 and 177 and associated reservoir 3 and 33, but share a common peristaltic pumping mechanism 4. The common peristaltic pumping mechanism 4 can have the ability to displace fluid in more than one tube, in a space-saving configuration. A first reservoir 3, first delivery tube 17 and first cannula 6 can be used to deliver the first therapeutic fluid (for example insulin), and a second reservoir 33, second delivery tube 177, and second cannula 66 can be used to deliver an additional therapeutic fluid, such as for example a second diabetic agent (for example an amylin analog like pramlintide) to the body. The different therapeutic fluids (e.g. insulin and pramlintide) can remain inside the separate tubing at all times. This feature prevents mixing of the fluids pumped from different reservoirs, thus sufficiently reducing the risk of contamination, and permitting control over the content and purity of the fluid delivered to the patient. The first cannula 6 and the second cannula 66) and the first reservoir 3 and second reservoir 33 can be located in the disposable part 2 while the pumping mechanism 4 can be located in the reusable part 1 of the dispensing patch unit 1010.

Figure 11:
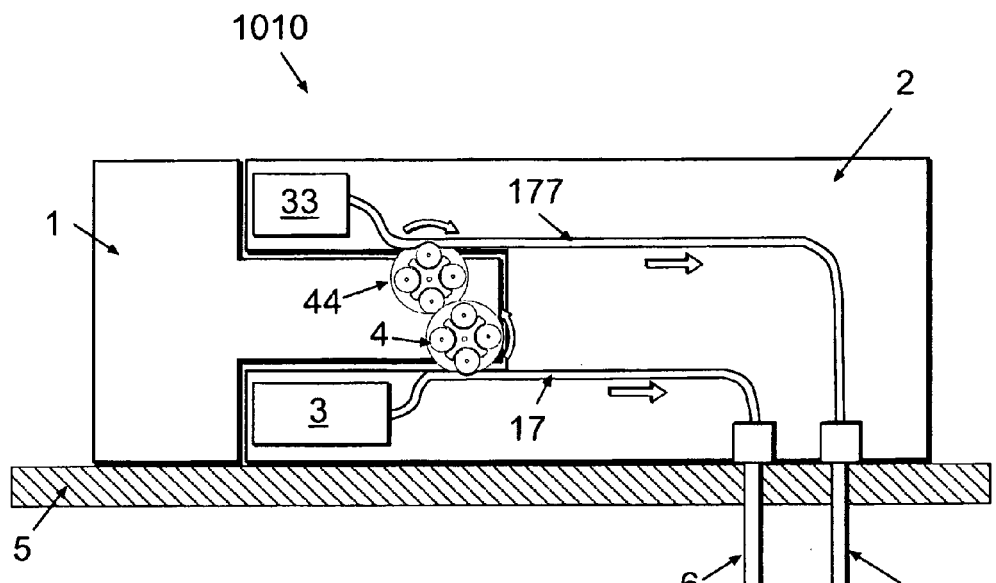
FIG. 11 is a schematic diagram that shows an insulin and pramlintide infusion device in which each fluid comprises an independent peristaltic pump, cannula, tube and associated reservoir.

FIG. 11 shows another implementation of a dispensing patch unit 1010, according to some preferred implementations, in which the pumping mechanism of both drugs is a peristaltic pump. Each therapeutic fluid delivery path can include an independent peristaltic pumping mechanism 4 and 44 and associated cannula 6 and 66, delivery tube 17 and 177, and reservoir 3 and 33. The cannulae 6 and 66 and reservoirs 3 and 33 can be located in the disposable part 2 and the pumps 4 and 44 can be located in the reusable part 1 of the dispensing patch unit 1010. In some optional variations, the pumping mechanism applied for delivery of each of the fluids (for example insulin and pramlintide) can be a piston-type displacement type reservoir. In some implementations, the pumping mechanism of both drugs can include shared components such as gears, motor (e.g. stepper motor, DC motor etc.), and the like. Using the same component or components for activating both of the pumping mechanisms can simplify control and/or monitoring procedures related to the activity of the pumping mechanism, such as for example fault detection (e.g. motor malfunctioning, occlusion, leaks, etc.), metering the amount of delivered fluid, and the like. In some optional variations, the pumping mechanisms applied for delivery of each of the fluids can be separate and therefore not include shared components.

Figure 12:
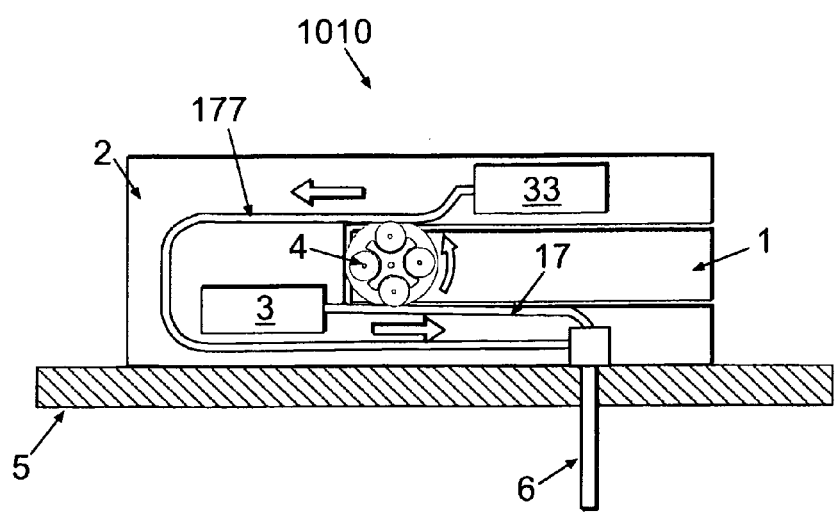
FIG. 12 is a schematic diagram that shows an insulin and pramlintide infusion device in which each fluid comprises an independent tube and associated reservoir, but share a common peristaltic pump and cannula.

FIG. 12 shows another implementation of a dispensing patch unit 1010 in which the driving mechanism of both therapeutic fluids is a peristaltic pump. Each therapeutic fluid delivery path can include an independent delivery tube 17 and 177 and associated reservoir 3 and 33, but share a common peristaltic pump 4 and cannula 6. The cannula 6 and reservoirs 3 and 33 can be located in the disposable part 2 and the pumping mechanism 4 can be located in the reusable part 1 of the dispensing patch unit 1010.

FIG. 13 shows a device that includes a dispensing apparatus and a sensing apparatus in which blood glucose and/or other body chemistry or condition readings can be received from a subcutaneous monitor 1006 (for example a glucose monitor). The subcutaneous monitor 1006 can in some variations provide continuous, semi-continuous, or periodic data. The dispensing patch unit 1010 can include a first cannula 6 and a second cannula 66 each that penetrate the skin 5 to allow separate delivery of two therapeutic fluids (for example insulin and an amylin analog like pramlintide). Communication between the continuous subcutaneous monitor 1006 and the remote control unit 1008 can be provided, allowing programming, data handling, and user inputs.

Figure 13A:
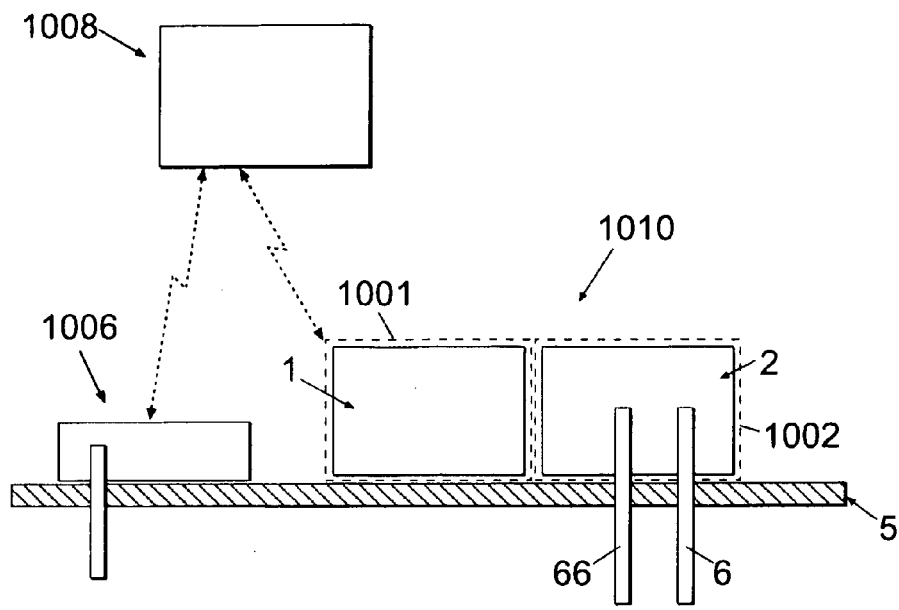
FIG. 13a and FIG. 13b are schematic diagrams that show insulin and pramlintide infusion devices containing examples of continuous subcutaneous glucose monitors providing blood glucose readings (BG)
Figure 13B:
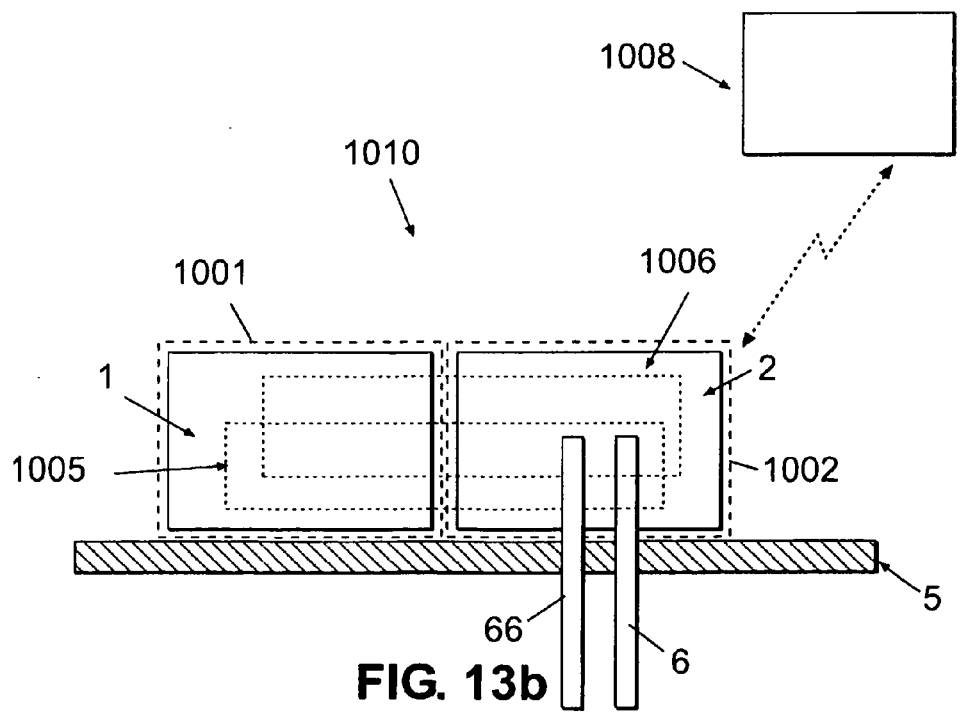

FIG. 13a shows an implementation in which a current blood glucose (BG) value is measured by an independent subcutaneous glucose monitor 1006 that can in some implementations be a continuous or semi-continuous monitor. FIG. 13b shows an implementation in which the subcutaneous glucose sensing (monitoring) apparatus (1006) is integrated within the dispensing patch unit 1010 of the therapeutic fluid delivery device. The therapeutic fluid dispensing apparatus 1005 and glucose sensing apparatus 1006 constitute a single delivery device. Sensing of blood glucose can be carried out via the insulin infusion cannula 6 or the pramlintide infusion cannula 66 if the device is used for diabetes control and treatment. Single cannula for both dispensing and sensing is described in detail in U.S. application Ser. No. 11/706,606 which is incorporated herein by reference in its entirety.

Alternatively, the sensing apparatus and the dispensing apparatus can have separate cannulae that penetrate the skin 5 and reside in the subcutaneous tissue. The delivery device of this implementation can optionally include two parts—a reusable part 1 and a disposable part 2, where each part can have a corresponding housing 1001 and 1002.

Figure 14:
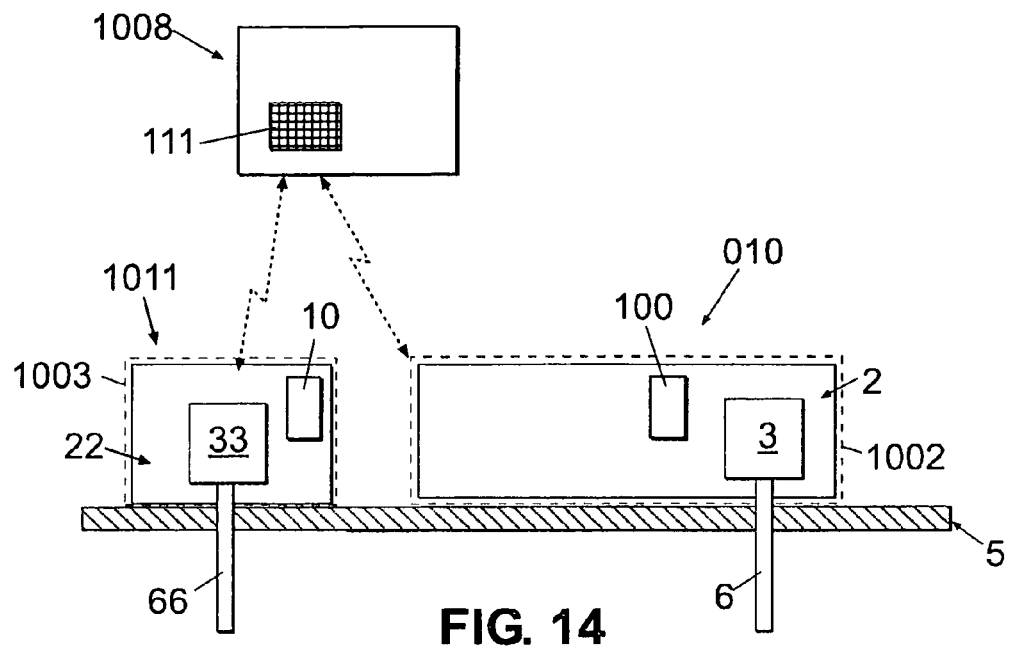
FIG. 14 is a schematic diagram that shows a device including an infusion patch unit for a first therapeutic fluid (such as for example insulin), an infusion patch unit for a second therapeutic fluid (such as for example pramlintide), and a remote control unit that communicates with both patch units.

FIG. 14 shows another implementation in which the device comprises a first therapeutic fluid (for example insulin) dispensing patch unit 1010, an additional dispensing patch unit 1011 that delivers another injectable therapeutic fluid to the subcutaneous tissue (such as for example an amylin analog like pramlintide), and a remote control unit 1008, which communicates with at least one and preferably both patch units 1010 and 1011, allowing programming, user inputs and data acquisition. Manual inputs can be carried out by button switches 10 located on either patch unit 1010 and 1011. Each patch unit 1010 and 1011 contains a reservoir 3 and 33 and a cannula 6 and 66 that penetrates the skin 5. Each patch unit 1010 and 1011) is contained in a different housing 1002 and 1003 and can include a disposable part 2 and 22. Moreover, the patch units 1010 and 1011 can be directly attached to the user's skin 5 by adhesive or other attachment means or can be attached to a dedicated cradle unit that is adherable to the user's skin 5 and allows connection and disconnection of the patch units 1010 and 1011.

Figure 15:
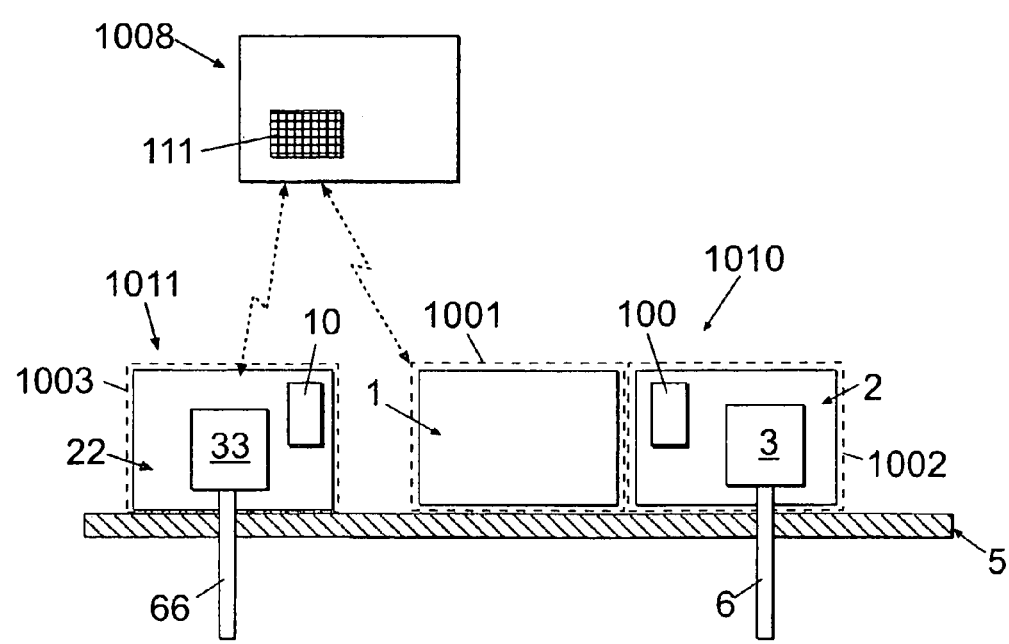
FIG. 15 is a schematic diagram that shows a device including a first infusion patch unit composed of disposable and reusable parts, a second infusion patch unit, and a remote control unit that communicates with both patch units; and FIG. 16a, FIG. 16b.

FIG. 15 shows another implementation in which the device comprises one therapeutic fluid (e.g. insulin) dispensing patch unit 1010 that includes a disposable part 2 and a reusable part 1, an additional dispensing patch unit 1011 that delivers another injectable therapeutic fluid to the subcutaneous tissue (e.g. pramlintide), and a remote control unit 1008 that communicates with at least one and preferably both patch units 1010 and 1011 thereby allowing programming, user inputs and data acquisition. Manual inputs can be carried out by buttons switches 10 and 100 located on patch units 1011 and 1010, accordingly. Each patch unit contains a reservoir 3 and 33 and a cannula 6 and 66 that penetrates the skin 5. The patch units 1010 and 1011 can be directly attached to the user's skin 5 by adhesive or other attachment means or can be attached to a dedicated cradle unit that is adherable to the user's skin 5 and allows connection and disconnection of the patch units 1010 and 1011. The first therapeutic fluid (e.g. insulin) dispensing patch unit 1010 can be composed of two housings 1001 and 1002 that include reusable 1 and disposable 2 parts, respectively. The relatively cheap components of the device reside in the disposable part 2 (e.g. reservoir 3) and the relatively expensive components reside in the reusable part 1. Similarly, the second therapeutic (e.g. pramlintide) patch unit 1011 can optionally include a disposable part 22 contained within one housing 1003.

For the devices in FIG. 14 and FIG. 15, therapeutic fluids (e.g. pramlintide and/or insulin) dosages can be delivered by the patch units 1010 and 1011 via instructions received from the remote control unit 1008 of the device. The user can optionally command administration of any therapeutic fluid dosage by inputting the value(s) into the remote control unit. Alternatively the user can select a number of quanta of either therapeutic fluid to be delivered, and/or the user may select the dosages from within a grid 111.

Figure 16A:
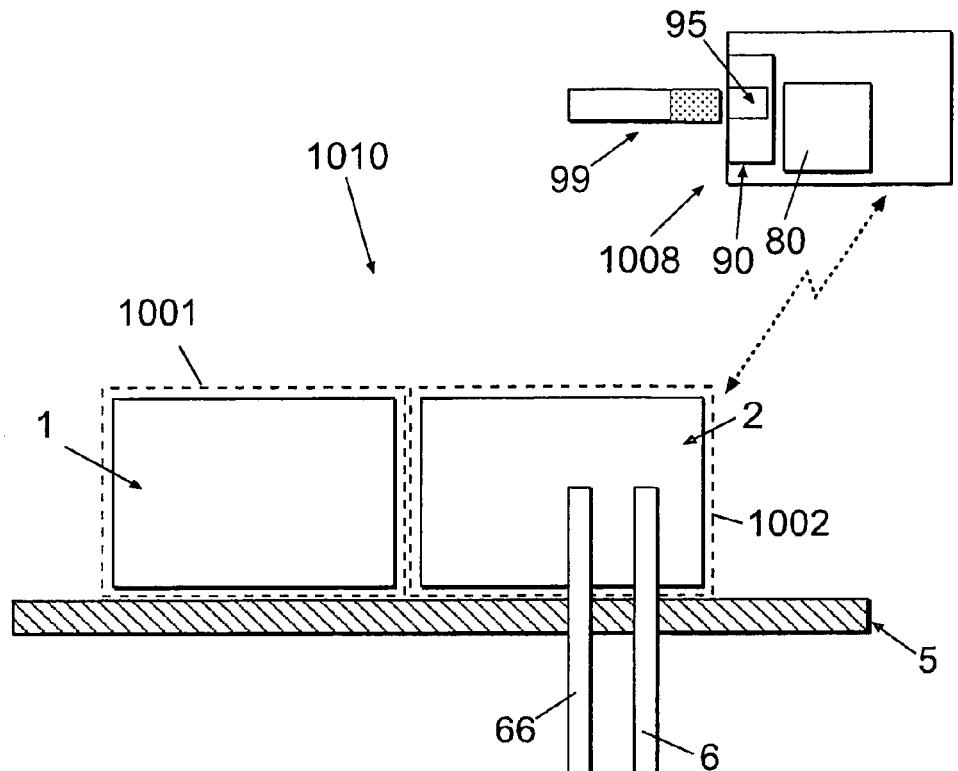
FIG. 16c is a schematic diagram that shows three different configurations of an infusion device for delivering two therapeutic fluids including a remote control, infusion patch and a blood glucose monitor.
Figure 16B:
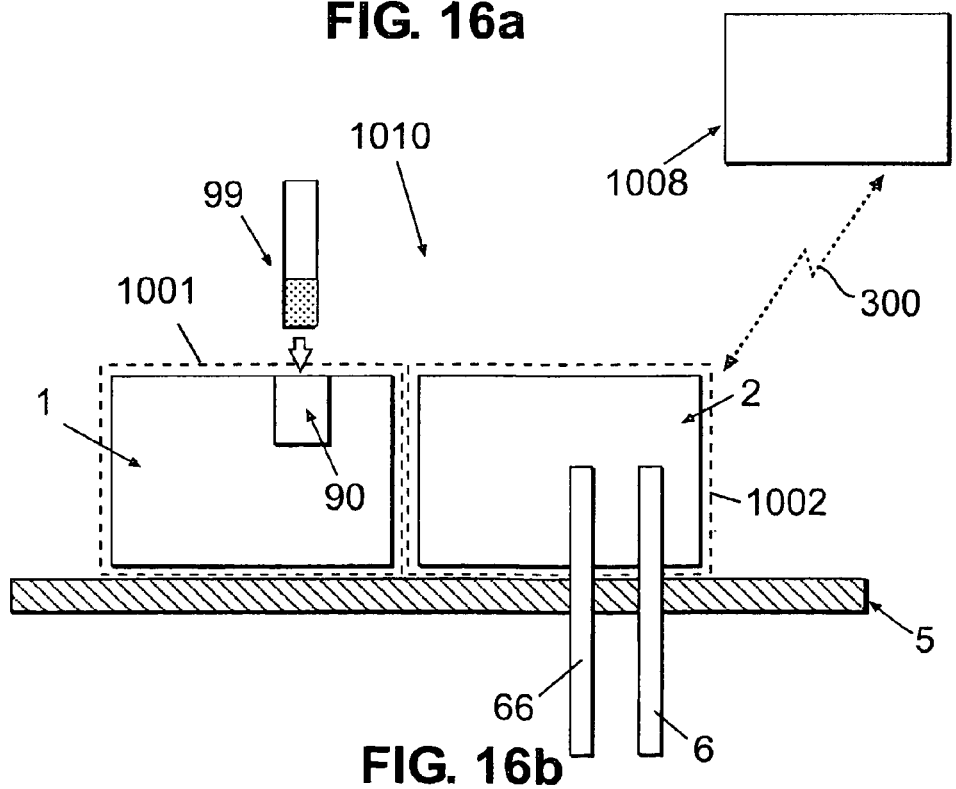
Figure 16C:
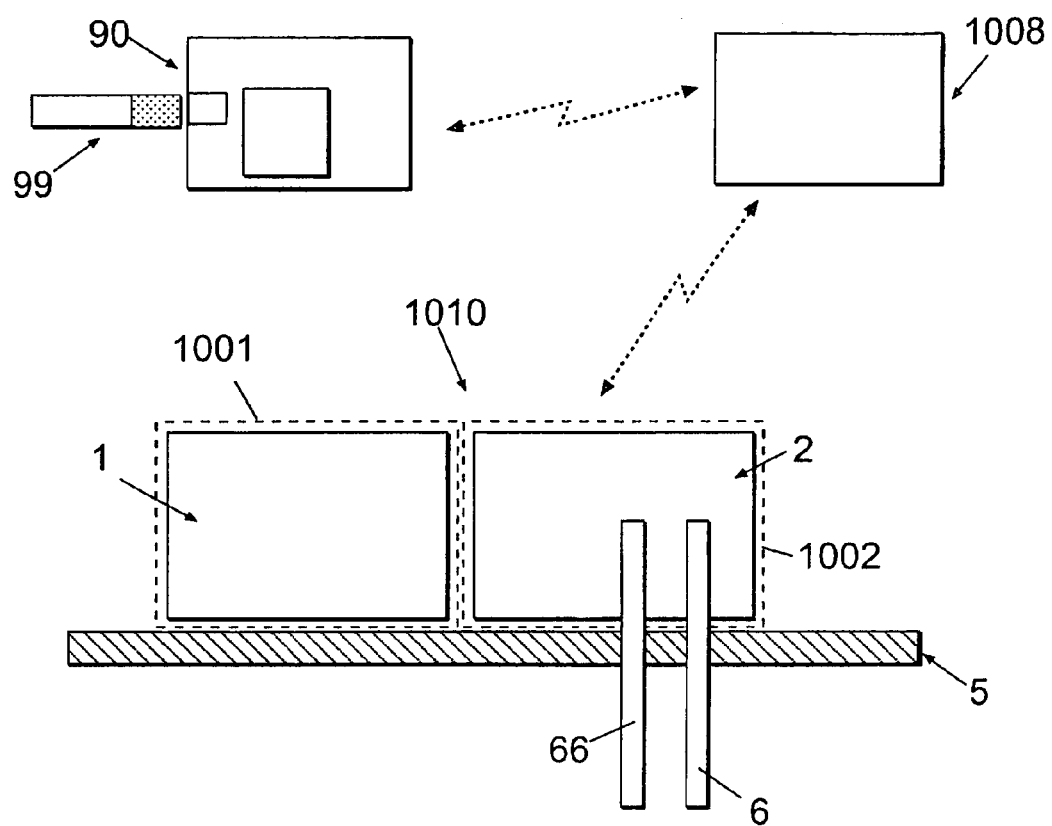

FIG. 16a, FIG. 16b, and FIG. 16c show three possible implementations of devices that each contains a glucometer 90 that can provide blood glucose (BG) inputs. FIG. 16a shows a glucometer 90 located in the remote control unit 1008 of the device, which includes an opening 95 for receiving of a test strip 99. The user extracts blood from the body, places a blood drop on the test strip 99 and inserts the strip 99 into the opening 95. The glucose readings are displayed on a screen 80 of the remote control unit 1008.

FIG. 16b shows a glucometer 90 that is located in the reusable part 1 of the dispensing patch unit 1010. Communication 300 between the glucometer 90 residing in the dispensing patch unit 1010 and the remote control unit 1008 can be provided, thereby allowing programming, data handling, and user inputs. FIG. 16c shows an implementation in which glucose readings are 90 received from an independent glucometer. It should readily be recognized that while the implementations shown in FIG. 16a, FIG. 16b, and FIG. 16c are discussed with regards to glucose monitoring for a diabetic patient, other types of sensing monitors can be substituted while remaining within the scope of the currently disclosed subject matter.

The subject matter described herein may be embodied in systems, apparatus, methods, and/or articles depending on the desired configuration. In particular, various features or implementations of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device. Such computer programs (also known as programs, software, software applications, applications, components, or code) include machine instructions for a programmable processor, and may be implemented in a high-level procedural and/or object-oriented programming language, and/or in assembly/machine language. As used herein, the term "machine-readable medium" refers to any tangible computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, one or more features or implementations of the subject matter described herein may be implemented on a computer or computing device having a display device (e.g., a CRT (cathode ray tube) or LCD (liquid crystal display) monitor) for displaying information to the user and a keyboard and a pointing device (e.g., a mouse or a trackball) by which the user may provide input to the computer. Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input, such as for example using one or more physical buttons and/or a touch-sensitive screen.

Although a few variations have been described in detail above, other modifications or additions are possible. The implementations set forth in the foregoing description do not represent all implementations consistent with the subject matter described herein. Instead, they are merely some examples consistent with aspects related to the described subject matter. In particular, further features and/or variations may be provided in addition to those set forth herein. For example, the implementations described above may be directed to various combinations and subcombinations of the disclosed features and/or combinations and subcombinations of several further features disclosed above. In addition, the logic flow depicted in the accompanying figures and/or described herein do not require the particular order shown, or sequential order, to achieve desirable results. Other embodiments may be within the scope of the following claims.

What is claimed is:

1. A portable ambulatory, skin securable therapeutic fluid delivery device for a user, the device comprising:
    a disposable part housing accommodating at least a first reservoir containing a first therapeutic fluid and a second reservoir containing a second therapeutic fluid;
    a reusable part housing accommodating a first pumping mechanism, a second pumping mechanism and a processor, said disposable part housing being removably coupleable to the reusable part housing, wherein the first pumping mechanism delivers the first therapeutic fluid from the first reservoir and the second pumping mechanism delivers the second fluid from the second reservoir, wherein the first and second pumping mechanisms have one or more shared parts, wherein the one or more shared parts comprise a gear and/or a motor;
    a first cannula configured to be in fluid communication with the first reservoir, the first cannula being further configured to penetrate skin of the user to subcutaneously deliver the first therapeutic fluid; and
    a second cannula configured to be in fluid communication with the second reservoir, the second cannula being further configured to penetrate the skin of the user to subcutaneously deliver the second therapeutic fluid,
    wherein upon coupling of the reusable part housing and the disposable part housing the first and second pumping mechanisms are controlled by the processor to deliver concomitantly the first therapeutic fluid from the first reservoir to the first cannula at a first dosing rate and the second therapeutic fluid from the second reservoir to the second cannula at a second dosing rate.

2. The device as in claim 1, wherein the first dosing rate is different from the second dosing rate.

3. The device as in claim 1, further comprising a sensing apparatus in communication with the processor for determining an analyte concentration of the user.

4. The device as in claim 3, wherein the sensing apparatus determines glucose concentration data and communicates the glucose concentration data to the processor, in which the processor controls the first and/or the second dosing rate in response to the glucose concentration data.

5. The device as in claim 3, wherein the processor, the first and second pumping mechanisms and the sensing apparatus operate in one of: a closed loop manner, a semi-closed loop manner, and an open loop manner.

6. The device as in claim 1, wherein the first therapeutic fluid comprises insulin.

7. The device as in claim 6, wherein the second therapeutic fluid comprises an amylin analog.

8. The device as in claim 7, wherein the amylin analog comprises pramlintide acetate.

9. The device as in claim 6, wherein the second therapeutic fluid comprises a glucagon.

10. The device as in claim 6, wherein the second therapeutic fluid comprises an exenatide.

11. The device as in claim 6, wherein the second therapeutic fluid comprises incretin mimetic.

12. The device as in claim 6, wherein the second therapeutic fluid comprises a biological active compound that complements the effects of insulin and being used as an adjunctive therapy to insulin delivery to alleviate postprandial glucose excursions.

13. The device as in claim 1, wherein a second dosing range is based on the first dosing rate.

14. The device as in claim 6, where in the second dosing rate is associated with an insulin total daily dose (TDD).

15. The device as in claim 1, wherein the first and/or second dosing rate is based on expected calorie and/or carbohydrate intake by the user.

16. The device as in claim 1, further comprising:
a cradle that comprises a first side adherable to the skin and a second side configured for connection and disconnection of at least the disposable part housing.

17. The device as in claim 16, wherein the cradle is configured to receive therethrough the first and second cannula.

18. The device as in claim 1, wherein at least one of the first and the second reservoirs is collapsible such that it changes volumes according to the volume of the therapeutic fluid contained therein.

19. The device as in claim 1, further comprising one or more buttons via which the user selects adjusting the first and/or second dosing rate.

20. A portable ambulatory, skin adherable infusion device for delivery of insulin and a therapeutic fluid to a user, the device comprising:
a disposable part housing accommodating at least a first reservoir containing insulin and a second reservoir containing a therapeutic fluid, said therapeutic fluid comprising at least one of: an amylin analog, a glucagon, an exenatide and incretin mimetic;
a first cannula configured to be in fluid communication with the first reservoir, the first cannula being further configured to penetrate a user's skin to subcutaneously deliver the insulin;
a second cannula configured to be in fluid communication with the second reservoir, the second cannula being further configured to penetrate the user's skin to subcutaneously deliver the therapeutic fluid; and
a reusable part housing accommodating a peristaltic pump and a processor, said disposable part housing being removably coupleable to the reusable part housing,
wherein upon coupling of the reusable part housing and the disposable part housing said peristaltic pump is controlled by the processor to deliver concomitantly the insulin from the first reservoir to the first cannula at a first dosing rate and the therapeutic fluid from the second reservoir to the second cannula at a second dosing rate.

21. A method for delivery of insulin and a therapeutic fluid to a body of a user using a portable ambulatory, skin securable device, the method comprising:
applying to the body of the user a portable ambulatory, skin securable device which includes:
a disposable part housing accommodating at least a first reservoir containing insulin and a second reservoir containing a therapeutic fluid, said therapeutic fluid comprising at least one of: an amylin analog, a glucagon, an exenatide and incretin mimetic,
a reusable part housing accommodating a first pumping mechanism, a second pumping mechanism and a processor, said disposable part housing being removably coupled to the reusable part housing, wherein the first pumping mechanism delivers the insulin from the first reservoir and the second pumping mechanism delivers the therapeutic fluid from the second reservoir, wherein the first and second pumping mechanisms have one or more shared parts, wherein the one or more shared parts comprise a gear and/or a motor,
a first cannula configured to be in fluid communication with the first reservoir, the first cannula being further configured to penetrate a user's skin to subcutaneously deliver the insulin, and
a second cannula configured to be in fluid communication with the second reservoir, the second cannula being further configured to penetrate the user's skin to subcutaneously deliver the therapeutic fluid;
controlling via the processor the first and second pumping mechanisms delivering concomitantly the insulin from the first reservoir to the first cannula at a first dosing rate and the therapeutic fluid from the second reservoir to the second cannula at a second dosing rate;
adjusting the second dosing rate based on data related to the insulin or to the first dosing rate; and
administering, via the first cannula and second cannula, concomitantly the insulin at the first dosing rate and said therapeutic fluid at the second dosing rate to the body of a user.

22. The method of claim 21, wherein the first dosing rate includes an insulin bolus component and adjusting of the first dosing rate including reducing the insulin bolus component.

23. The method of claim 21, wherein data related to the insulin or to the first dosing rate includes a percentage of an insulin total daily dose (TDD).

24. The method of claim 21, further comprising determining a tolerability of the user to insulin and/or the therapeutic fluid.

25. The method of claim 21, wherein the data related to insulin or to the first dosing rate is selected from a group consisting of: consumable intake, amount of carbohydrates to be consumed, glycemic intake, body glucose level, whether the user is a first-time user.

26. The method of claim 21, wherein the administering the insulin and the therapeutic fluid occurs prior to a meal intake by the user.

27. The method of claim 21, wherein the therapeutic fluid is administered in a predetermined time interval.

28. A portable ambulatory, skin securable therapeutic fluid delivery device for a user, the device comprising:
a disposable part housing accommodating at least a first reservoir containing a first therapeutic fluid and a second reservoir containing a second therapeutic fluid;

a reusable part housing accommodating a first pumping mechanism, a second pumping mechanism and a processor, said disposable part housing being removably coupleable to the reusable part housing, wherein the first pumping mechanism delivers the first therapeutic fluid from the first reservoir and the second pumping mechanism delivers the second fluid from the second reservoir, wherein the first and second pumping mechanisms have one or more shared parts, wherein the one or more shared parts comprise a gear and/or a motor; and at least one cannula configured to be in fluid communication with the first and second reservoirs, the at least one cannula being further configured to penetrate skin of the user to subcutaneously deliver both the first therapeutic fluid and the second therapeutic fluid, wherein upon coupling of the reusable part housing and the disposable part housing the first and second pumping mechanisms are controlled by the processor to deliver concomitantly the first therapeutic fluid from the first reservoir to the at least one cannula at a first dosing rate and the second therapeutic fluid from the second reservoir to the at least one cannula at a second dosing rate.

29. A portable ambulatory, skin adherable infusion device for delivery of insulin and a therapeutic fluid to a user, the device comprising:

a disposable part housing accommodating at least a first reservoir containing insulin and a second reservoir containing a therapeutic fluid, said therapeutic fluid comprising at least one of: an amylin analog, a glucagon, an exenatide and incretin mimetic;

at least one cannula configured to be in fluid communication with the first and second reservoirs, the at least one cannula being further configured to penetrate skin of the user to subcutaneously deliver both the insulin and the therapeutic fluid; and a reusable part housing accommodating a peristaltic pump and a processor, said disposable part housing being removably coupleable to the reusable part housing, wherein upon coupling of the reusable part housing and the disposable part housing said peristaltic pump is controlled by the processor to deliver concomitantly the insulin from the first reservoir to the at least one cannula at a first dosing rate and the therapeutic fluid from the second reservoir to the at least one cannula at a second dosing rate.

30. A method for delivery of insulin and a therapeutic fluid to a body of a user using a portable ambulatory, skin securable device, the method comprising:

applying to the body of the user a portable ambulatory, skin securable device which includes:

a disposable part housing accommodating at least a first reservoir containing insulin and a second reservoir containing a therapeutic fluid, said therapeutic fluid comprising at least one of: an amylin analog, a glucagon, an exenatide and incretin mimetic, a reusable part housing accommodating a first pumping mechanism, a second pumping mechanism and a processor, said disposable part housing being removably coupled to the reusable part housing, wherein the first pumping mechanism delivers the insulin from the first reservoir and the second pumping mechanism delivers the therapeutic fluid from the second reservoir, wherein the first and second pumping mechanisms have one or more shared parts, wherein the one or more shared parts comprise a gear and/or a motor, and at least one cannula configured to be in fluid communication with the first and second reservoirs, and being further configured to penetrate skin of the user to subcutaneously deliver the insulin and the therapeutic fluid;

controlling via the processor the first and second pumping mechanisms delivering concomitantly the insulin from the first reservoir to the at least one cannula at a first dosing rate and the therapeutic fluid from the second reservoir to the at least one cannula at a second dosing rate;

adjusting the second dosing rate based on data related to the insulin or to the first dosing rate; and administering, via the at least one cannula, concomitantly the insulin at the first dosing rate and said therapeutic fluid at the second dosing rate to the body of a user.

* * * * *

UNITED STATES PATENT AND TRADEMARK OFFICE
CERTIFICATE OF CORRECTION

PATENT NO.          : 9,173,991 B2
APPLICATION NO.     : 12/452484
DATED               : November 3, 2015
INVENTOR(S)         : Ofer Yodfat et al.

Page 1 of 1

It is certified that error appears in the above-identified patent and that said Letters Patent is hereby corrected as shown below:

In the specification

Col. 9, Line 9,
   "pressing of the manual button 10), the delivered dose can" should read
   --pressing of the manual button 10, the delivered dose can--;

Col. 13, Line 23,
   "The first cannula 6 and the second cannula 66) and the first" should read
   --The first cannula 6 and the second cannula 66 and the first--; and Col. 14, Line 40,
   "1010 and 1011) is contained in a different housing 1002 and" should read
   --1010 and 1011 is contained in a different housing 1002 and--.

Signed and Sealed this
Fifth Day of July, 2016

Michelle K. Lee
*Director of the United States Patent and Trademark Office*